(12) United States Patent
Bransky et al.

(10) Patent No.: US 9,625,357 B2
(45) Date of Patent: Apr. 18, 2017

(54) DISPOSABLE CARTRIDGE FOR PREPARING A SAMPLE FLUID CONTAINING CELLS FOR ANALYSIS

(75) Inventors: Avishay Bransky, Kyriat Tivon (IL); Liron Shlomo, Kibbutz Shomrat (IL)

(73) Assignee: PIXCELL MEDICAL TECHNOLOGIES LTD., Yokneam Llit (IL)

( * ) Notice: Subject to any disclaimer, the term of this patent is extended or adjusted under 35 U.S.C. 154(b) by 697 days.

(21) Appl. No.: 14/003,189

(22) PCT Filed: Mar. 8, 2012

(86) PCT No.: PCT/IL2012/000120
§ 371 (c)(1),
(2), (4) Date: Oct. 22, 2013

(87) PCT Pub. No.: WO2012/120506
PCT Pub. Date: Sep. 13, 2012

(65) Prior Publication Data
US 2014/0033809 A1 Feb. 6, 2014

Related U.S. Application Data

(60) Provisional application No. 61/450,661, filed on Mar. 9, 2011.

(51) Int. Cl.
*G01N 1/00* (2006.01)
*G01N 1/20* (2006.01)
*B01L 3/00* (2006.01)

(52) U.S. Cl.
CPC ........ *G01N 1/2035* (2013.01); *B01L 3/50273* (2013.01); *B01L 3/502738* (2013.01);
(Continued)

(58) Field of Classification Search
CPC B01L 2400/0683; G01N 33/18; G01N 11/00; G01N 33/4905; G01N 33/2823;
(Continued)

(56) References Cited

U.S. PATENT DOCUMENTS

| 4,065,263 | A | 12/1977 | Woodbridge |
| 2001/0053549 | A1* | 12/2001 | McHale ............ A61K 9/0009 435/446 |

(Continued)

FOREIGN PATENT DOCUMENTS

| CN | 1608735 A | 4/2005 |
| CN | 102105227 A | 6/2011 |

(Continued)

OTHER PUBLICATIONS

Chinese Office Action from Intellectual Property Office of China for Application No. 20128001831.8, dated Jan. 18, 2016, 8 pages.

(Continued)

*Primary Examiner* — John Fitzgerald
*Assistant Examiner* — Truong Phan
(74) *Attorney, Agent, or Firm* — Greenblum & Bernstein, P.L.C.

(57) ABSTRACT

The invention discloses a disposable cartridge for preparing a sample fluid containing cells for analysis. The cartridge comprises one or more parallel preparation units, each preparation unit comprises one or more chambers enclosed between seals and connected in series. Each chamber is configured for receiving an input fluid, performing a procedure affecting the fluid thereby generating an output fluid, and releasing the output fluid. A first chamber of the one or more chambers is a pressable chamber coupled to a first opening, while a last chamber of the one or more chambers is coupled to a second opening. The input fluid of the first chamber is the sample fluid. The one or more preparation (Continued)

units are coupleable to a compartment for performing analysis of the respective output fluids convey able via the second openings.

26 Claims, 13 Drawing Sheets

(52) U.S. Cl.
CPC . *B01L 3/502723* (2013.01); *B01L 2200/0621* (2013.01); *B01L 2200/0689* (2013.01); *B01L 2300/044* (2013.01); *B01L 2300/087* (2013.01); *B01L 2300/123* (2013.01); *B01L 2400/0481* (2013.01); *B01L 2400/0683* (2013.01)

(58) Field of Classification Search
CPC ............. G01N 29/024; G01N 33/2847; G01N 27/223; G01N 33/1833; G01N 31/222; G01N 30/32; G01N 30/34; G01N 30/36
USPC ..... 73/64.56, 53.01, 61.41, 61.43; 435/287.2
See application file for complete search history.

(56) References Cited

U.S. PATENT DOCUMENTS

| | | | |
|---|---|---|---|
| 2004/0047769 A1 | 3/2004 | Tanaami | |
| 2005/0196855 A1 | 9/2005 | Gau et al. | |
| 2006/0054226 A1* | 3/2006 | Yamazaki | B01L 3/502738 137/827 |
| 2007/0292858 A1* | 12/2007 | Chen | B01L 3/502 435/6.18 |
| 2008/0277370 A1* | 11/2008 | Mikkelsen | D06F 39/022 215/247 |
| 2009/0074626 A1 | 3/2009 | Kadel et al. | |
| 2009/1021507 | 8/2009 | McDevitt et al. | |
| 2009/0253215 A1* | 10/2009 | Hikmet | B01L 3/50273 436/174 |
| 2010/0105735 A1* | 4/2010 | Palmer | A61J 7/0038 514/326 |
| 2010/0304986 A1 | 12/2010 | Chen et al. | |
| 2010/0317093 A1* | 12/2010 | Turewicz | B01L 3/50273 435/287.2 |
| 2010/0323432 A1 | 12/2010 | Asogawa et al. | |

FOREIGN PATENT DOCUMENTS

| | | |
|---|---|---|
| JP | 59-54968 | 3/1984 |
| JP | 5-261270 | 10/1993 |
| JP | 2002-365299 | 12/2002 |
| JP | 2005-21866 | 1/2005 |
| JP | 2005-37368 | 2/2005 |
| JP | 2005-313065 | 11/2005 |
| WO | WO 2008076395 | 6/2008 |
| WO | 2009/035061 | 3/2009 |

OTHER PUBLICATIONS

International Search Report from the European Patent Office for International Application No. PCT/IL2012/000120, mailed Feb. 5, 2013.
Written Opinion of the International Searching Authority for International Application No. PCT/IL2012/000120, mailed Feb. 5, 2013.
English language translation of JP Application No. 2013-557222, dated Jun. 21, 2016.
Office Action issued in China Counterpart Patent Appl. No. 201280011831.8, dated Sep. 12, 2016.

* cited by examiner

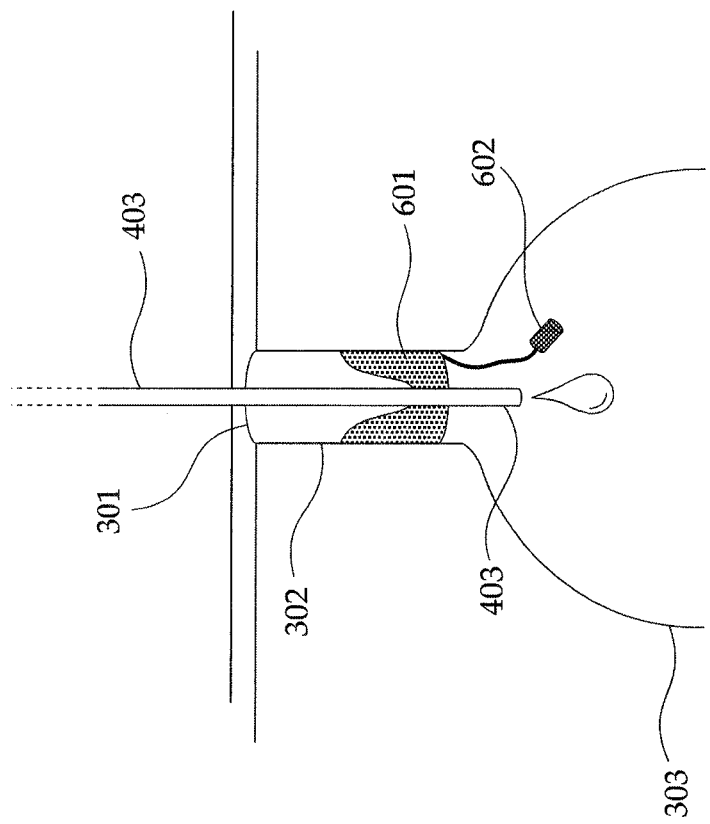
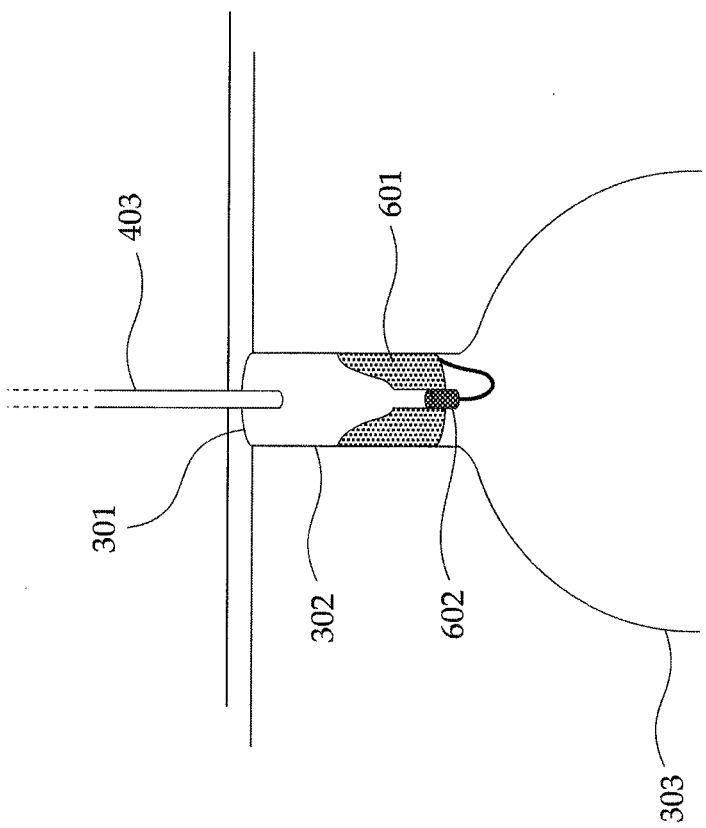
FIGURE 6A
FIGURE 6B

DISPOSABLE CARTRIDGE FOR PREPARING A SAMPLE FLUID CONTAINING CELLS FOR ANALYSIS

CROSS REFERENCE TO RELATED APPLICATIONS

This application is a national phase application based on PCT/IL2012/000120, filed Mar. 8, 2012, and claims the benefit of U.S. Provisional Application No. 61/450,661, filed Mar. 9, 2011, the contents of both of which are incorporated herein by reference.

FIELD OF THE INVENTION

The invention relates to the field of performing automatic analysis of fluids. More specifically, it relates to a cartridge for preparing a sample fluid containing cells for analysis.

BACKGROUND OF THE INVENTION

Point-of-care testing (POCT) is defined as medical testing at or near the site of patient care, for example at the doctor's office. Point of Care Testing systems enable quick performance of tests, for example blood tests, eliminating a need for sending samples to laboratory. Quick obtaining of test results allows immediate clinical management decisions to be made.

It is desirable that such POCT systems be simple to use and require minimal maintenance. To that end, some systems use fully self-contained disposable cartridges or strips. In fully-automated systems, no preliminary sample preparation is required and the cartridges eliminate the risk of contamination.

U.S. Pat. No. 7,347,617 by Pugia et al., entitled "Mixing in Microfluidic Devices", published in 2008, discloses mixing of liquids in a microfluidic device, by dispensing the liquids into a first chamber to produce combined liquid. The liquids are thereafter discharged through at least one capillary from the first chamber into a second chamber for complete mixing.

U.S. Pat. No. 4,030,888 by Yamamoto et al., entitled "Automatic Blood Analyzer", published in 1977, discloses a fully automatic system for determining the seven blood parameters. The flow of a diluent and the blood solution starting from the introduction of the sample, to counting portions, means for determination, and to the outlets are controlled by the supply of either vacuum or pneumatic pressure into two rotary proportioning cocks and chambers positioned upstream or downstream thereof.

U.S. Pat. No. 4,826,775 by Burns et al., entitled "Dilution Apparatus and Method", published in 1989, discloses an automatic dilution apparatus and method operable in conjunction with automated sample liquid analysis systems to automatically dilute sample liquids as supplied thereby to automated sample liquid analysis apparatus.

U.S. Pat. No. 4,908,187 by Kipke et al., entitled "Multi-Chambered Pump-Valve Device", published in 1990, discloses a diluting and mixing device which is capable of diluting a first solution to produce a second solution which is mixed with an undiluted third solution, to reproducibly produce a unique series of combined solutions. Each solution in said series of combined solutions may vary only in the concentration of a single (selected) reactant, and typically, each successive solution becomes increasingly more concentrated in the selected reactant. By employing a modification in procedure, each successive solution in said series may become decreasingly less concentrated in the selected reactant. This invention further relates to an automated system comprising the device connected to a stepping motor so as to rapidly and reproducibly produce said series of solutions, said device being further connected to an analyzer means for obtaining chemical, biochemical, or physical chemical data on said series of solutions.

U.S. Pat. No. 5,350,693 by Maimon et al., entitled "Multichamber Syringe Device for Fusing Cells", published in 1994, discloses an apparatus for fusing cells which includes a multichamber syringe having a first chamber containing a suspension of cells, a second chamber containing a suspension of cells, and a third chamber containing at least 40% by volume polyethylene glycol (PEG). The exit passageways of the chambers being braided such that the downstream ends thereof are beveled and face one another at the same level. The relative cross sections of the chambers being of a diameter such that a desired ratio of the suspensions and solution form in midair a mixture of 15% to 25% PEG by volume. The apparatus also includes a non-linear tube in fluid communication with the syringe for receiving the mixture therefrom and a device for causing a reciprocating passage of the mixture through the non-linear tube.

U.S. Pat. No. 5,380,491 by Carver Jr. et al., entitled "Apparatus for Pumping and Directing Fluids for Hematology Testing", published in 1995, discloses an apparatus for hematology testing, which has a sensing unit defining a counting orifice for the flow of a blood sample through the counting orifice to analyze the blood sample, and a pump unit having three syringes. A first syringe is coupled in fluid communication with the sensing unit on the inlet side of the counting orifice for injecting a stream of blood sample through the counting orifice. A second syringe is coupled in fluid communication with the sensing chamber on the inlet side of the counting orifice for simultaneously injecting a sheath of fluid surrounding the sample stream on the inlet side of the counting orifice. A third syringe is coupled to the sensing chamber on the outlet side of the counting orifice for aspirating a sheath of fluid from the sensing chamber surrounding the sample stream on the outlet side of the counting orifice.

U.S. Pat. No. 5,840,254 by Carver Jr. et al., entitled "Apparatus for Mixing Fluids for Analysis", published in 1998, discloses an apparatus for fluid analysis, such as hematologic analysis, a plurality of reagent-mixture components are each injected by a respective pump through a valve matrix and into a flow-injection unit. The flow-injection unit defines a mixing chamber including a plurality of protuberances or nubs projecting inwardly toward the center of the chamber, and spaced relative to each other both axially and radially. As the reagent-mixture components are injected into the mixing chamber, the nubs agitate the fluid flow and create turbulence, thereby dispersing the reagent-mixture components and in turn mixing the components together to create a reagent mixture. The flow rates of the reagent-mixture components are adjusted in order to select the reagent-mixture ratio as the components are combined in the flow-injection unit to thereby create the selected reagent mixture. Upon passage through the flow-injection unit, the reagent mixture is injected into a sensing unit for analyzing a particle distribution of the mixture.

U.S. Pat. No. 6,241,379 by Larsen et al., entitled "Micromixer Having a Mixing Chamber for Mixing two Liquids Through the Use of Laminar Flow," published in 2001, discloses a micromixer having a mixing chamber for mixing two fluids. The mixing chamber has a first inlet arrangement for the supply of a first fluid and a second inlet arrangement for the supply of a second fluid. The mixing chamber includes a wall along which the first fluid flows, and the second inlet arrangement has at least one opening in the wall. A projection is located on the wall adjacent to the opening and extending into the mixing chamber so that the first fluid flows around the projection and builds a boundary layer with the second fluid. Mixing takes place by diffusion through the boundary layer.

U.S. Pat. No. 6,537,813 by Chen et al., entitled "Concurrent Flow Mixing Methods and Apparatuses for the Preparation of Gene Therapy Vectors and Compositions Prepared Thereby", published in 2003, discloses methods adapted for making mixtures and condensate compositions. In the various embodiments, it provides controlled and uniform mixing of gene therapy vectors and gene therapy vector vehicles for improved reproducibility, scaleability, stability, and pharmaceutical efficacy.

U.S. Pat. No. 6,820,506 by Kipke et al., entitled "Multi-Chambered Pump-Valve Device", published in 2004, discloses a multi-chambered pump-valve device for performing chemical processes, detections or analyses is described herein. The device includes a plurality of chambers having variable volumes in fluid communication with one another via one or more passageways. Liquid may be directed through the device by merely changing the volumes of two or more chambers.

U.S. Pat. No. 6,877,892 by Karp et al., entitled "Multi-Stream Microfluidic Aperture Mixers", published in 2005, discloses a robust microfluidic mixing devices that mix multiple fluid streams passively, without the use of moving parts. In one embodiment, these devices contain microfluidic channels that are formed in various layers of a three-dimensional structure. Mixing may be accomplished with various manipulations of fluid flow paths and/or contacts between fluid streams.

U.S. Pat. No. 6,915,713 by Kipke et al., entitled "Multi-Chambered Pump-Valve Device", published in 2005, discloses a multi-chambered pump-valve device for performing chemical processes, detections or analyses. The device includes a plurality of chambers having variable volumes in fluid communication with one another via one or more passageways. Liquid may be directed through the device by merely changing the volumes of two or more chambers.

U.S. Pat. No. 6,979,569 by Carver Jr. et al., entitled "Apparatus and Method for Mixing Fluids for Analysis", published in 2005, discloses an apparatus for fluid analysis, a plurality of reagent-mixture components are each injected by a respective pump through a valve matrix and into a flow-injection unit. The flow-injection unit defines a mixing chamber including a plurality of. As the reagent-mixture components are injected into the mixing chamber, the nubs agitate the fluid flow, thereby dispersing the reagent-mixture components and in turn mixing the components together to create a reagent mixture. The flow rates of the reagent-mixture components are adjusted in order to select the reagent-mixture ratio as the components are combined in the flow-injection unit to thereby create the selected reagent mixture. Upon passage through the flow-injection unit, the reagent-mixture is injected into a sensing unit for analyzing a particle distribution of the mixture.

U.S. Pat. No. 7,314,060 by Chen et al., entitled "Fluid Flow Conducting Module", published in 2008, discloses a fluid flow conducting module comprising two or more inlets, one or more outlets, and a chamber that has a first and second blocks therein. Further, the chamber has a gradually wider section in the middle, and two convergent ends. One convergent end is connected to the inlets, and the other convergent end is connected to the outlets. The fluids are injected into the chamber through the inlets, flow through the chamber, and conducted towards one or more outlets for further collection and analysis.

PCT Publication WO/2009/053928 by Shany et al., entitled "Cartridge for a Biological Sample", published in 2009, discloses a sealed removable cartridge adapted for insertion into n assay device and adapted to contain a biologic sample, the cartridge comprising two or more assay locations adapted to facilitate, within said cartridge, two or more assays of said biologic sample; and an actuator interface adapted to interface with an actuator of said assay device, to transport said biologic sample towards at least one of said assay locations.

U.S. Pat. No. 5,096,669 by Lauks et al., entitled "Disposable sensing device for real time fluid analysis", published in 1992, discloses a system comprising a disposable device and hand held reader, which can perform a variety of electrochemical measurements on blood or other fluids. In operation, a fluid sample is drawn into the disposable device through an orifice by capillary action. The orifice is sealed off and the disposable device is inserted into the reader. The reader which controls the test sequence and flow of fluid causes a calibrant pouch located inside the device to be pierced, releasing the calibrant fluid to flow across the sensor arrays to perform calibration. Next an air bladder located in the device is depressed, forcing the sample across the sensors where measurements are performed and read by the reader which performs the calibrations. Once the measurements are made, the device can be withdrawn from the reader and discarded.

PCT Patent Application WO/2003/044488 by Berndtsson, entitled "Disposable apparatus for use in blood testing", published in 2003, discloses a disposable apparatus for use in blood testing adapted for simultaneous dilution of a blood sample into two different dilution ratios. A block-shaped housing has a first and a second receptacle; a first and a second cylinder, each having a piston moveable therein and each containing a defined volume of a diluent a valve including a valve body having three valve body channels extending therethrough and being positionable in three distinct positions. In one position the receptacles are put in simultaneous communication with one each of the cylinders through pairs of the channels. One of the receptacles as a first means for receiving a blood sample, is adapted to receive a blood sampling capillary tube.

PCT Patent Application WO/2003/104772 by Larsen, entitled "A disposable cartridge for characterizing particles suspended in a liquid" published in 2003, discloses a disposable cartridge for characterizing particles suspended in a liquid, especially a self-contained disposable cartridge for single-use analysis, such as for single-use analysis of a small quantity of whole blood. The self-contained disposable cartridge facilitates a straightforward testing procedure, which can be performed by most people without any particular education. Furthermore, the apparatus used to perform the test on the cartridge is simple, maintenance free, and portable.

PCT Patent Application WO/2006/084472 by Larsen entitled "Dual sample cartridge and method for characterizing particle in liquid" published in 2006, discloses an apparatus for characterizing particles suspended in a liquid, especially a self-contained disposable cartridge for single-use analysis, such as for single-use analysis of a small quantity of whole blood. Furthermore, the present invention relates to a method for characterizing particles in liquid and a device for sampling a small and accurate volume of liquid.

The apparatus comprises a housing having a mixing chamber and a collection chamber separated by a wall containing an opening, a first bore in the outer surface of the housing for entrance of a liquid sample, a first cavity for receiving and holding a first liquid sample, and a second cavity for receiving and holding a second liquid sample.

U.S. Pat. No. 6,016,712 by Warden and Kaplan, entitled "Device for receiving and processing a sample", published in 2000, discloses a device for receiving and processing a sample. The device comprises a sample receiving element adapted to establish fluid communication with and receive a sample directly from a sample container. The sample receiving element also allows for introduction of a sample into the device. A first chamber is in fluid communication with the sample receiving element. One or more second chambers are in fluid communication with the first chamber. The device also comprises first and second ports. The first port provides for venting the device. The second port provides for establishing communication between the device and means for moving the sample from the sample receiving element to the first chamber and for moving the sample from the first chamber to the one or more second chambers. Also included as part of the device is means for controlling the precise amount of the sample introduced into each of the second chambers. The first chamber and/or one or more of the second chambers are adapted for processing the sample. Also disclosed are kits containing the above devices and methods of using the devices to process a sample.

United States Patent Application 2006/0257993 by Mcdevitt et al., entitled "Integration of fluids and reagents into self-contained cartridges containing sensor elements", published in 2006, discloses an analyte detection device and method related to a portable instrument suitable for point-of-care analyses. In some embodiments, a portable instrument may include a disposable cartridge, an optical detector, a sample collection device and/or sample reservoir, reagent delivery systems, fluid delivery systems, one or more channels, and/or waste reservoirs. Use of a portable instrument may reduce the hazard to an operator by reducing an operator's contact with a sample for analysis. The device is capable of obtaining diagnostic information using cellular- and/or particle-based analyses and may be used in conjunction with membrane- and/or particle-based analysis cartridges. Analytes, including proteins and cells and/or microbes may be detected using the membrane and/or particle based analysis system.

United States Patent Application 2009/0215072 by Mcdevitt et al. entitled "Methods and compositions related to determination and use of white blood cell counts" published in 2009, discloses an analyte detection device and method related to a portable instrument suitable for point-of-care analyses. In some embodiments, a portable instrument may include a disposable cartridge, an optical detector, a sample collection device and/or sample reservoir, reagent delivery systems, fluid delivery systems, one or more channels, and/or waste reservoirs. Use of a portable instrument may reduce the hazard to an operator by reducing an operator's contact with a sample for analysis. The device is capable of obtaining diagnostic information using cellular- and/or particle-based analyses and may be used in conjunction with membrane- and/or particle-based analysis cartridges. Analytes, including proteins and cells and/or microbes may be detected using the membrane and/or particle based analysis system.

PCT Publication WO/2008/149365 by Leshansky et al., entitled "Systems and Methods for Focusing Particles", published in 2008, discloses a method of focusing particles. The method includes: providing a suspension of the particles in a suspending medium; and flowing the suspension along a channel, such that the flowing suspension occupies a certain volume that has at least one cross-sectional dimension smaller than 100 µm. The suspending medium has such viscoelastic properties, that flowing the suspension in the channel directs at least some of the particles towards a focus region, enclosed in said certain volume.

PCT Publication WO/2010/013238, by Bransky et al., entitled "Microfluidic System and Method for Manufacturing the Same", published in 2010, discloses a microfluidic system. The microfluidic system comprises a microchannel having in fluid communication with a fluid inlet for receiving a first fluid. The microfluidic system can further comprise a piezoelectric actuator which controls the flow of the first fluid in the microchannel by selectively applying external pressure on the wall of the microchannel.

SUMMARY OF THE INVENTION

It is one object of the invention to provide a disposable cartridge for preparing a sample fluid containing cells for analysis, the cartridge comprising:
one or more parallel preparation units, each preparation unit comprising:
one or more chambers enclosed between frangible seals and connected in series, wherein each chamber is configured for receiving an input fluid, performing a procedure affecting said fluid thereby generating an output fluid, and releasing said output fluid;
wherein a first chamber of said one or more chambers is a pressable chamber coupled to a first opening;
wherein a last chamber of said one or more chambers is coupled to a second opening; and
wherein the input fluid of said first chamber is said sample fluid;
wherein the one or more preparation units are coupleable to a compartment for performing analysis of the respective output fluids conveyable via the second openings.

According to one embodiment the invention provides a disposable wherein said one or more pressable chambers included in at least one of said one or more parallel preparation units include a single chamber being the first chamber and the last chamber in said one or more parallel preparation units.

According to another embodiment the invention provides a disposable wherein said one or more pressable chambers in said one or more parallel preparation units include each a respective substance.

According to another embodiment the invention provides a disposable cartridge wherein one or more of the chambers of at least one of said one or more preparation units include interconnected compartments.

According to another embodiment the invention provides a disposable cartridge, wherein the frangible seals enclosing a pressable chamber include a preceding frangible seal and a succeeding frangible seal.

According to another embodiment the invention provides a disposable cartridge, wherein in each one of said one or more parallel preparation units the preceding frangible seal of the first chamber prevents flow from said first chamber via said first opening.

According to another embodiment the invention provides a disposable cartridge, wherein in each one of said one or more parallel preparation units the succeeding frangible seal of the last chamber prevents flow from the respective preparation unit via said second opening.

According to another embodiment the invention provides a disposable cartridge, wherein in each one of said one or more parallel preparation units the first chamber is coupled to the first opening via a first channel.

According to another embodiment the invention provides a disposable cartridge, wherein the preceding seal of said first chamber is configured for preventing fluid from flowing via a space generatable between inner surface of said first channel and a carrier usable to introduce the sample fluid into said first chamber.

According to another embodiment the invention provides a disposable cartridge, wherein the preceding seal of said first chamber comprises:
 a first frangible seal configured for preventing flow from said first chamber via said first opening prior to introducing the sample fluid into said first chamber by the carrier; and
 a second seal configured for preventing fluid from flowing via the space subsequent to introducing the sample fluid.

According to another embodiment the invention provides a disposable cartridge, wherein in each one of said one or more parallel preparation units the preceding frangible seal of said first pressable chamber is configured to be broken by a carrier usable to introduce the sample fluid into said first chamber.

According to another embodiment the invention provides a disposable cartridge, wherein in each one of said one or more parallel preparation units the preceding frangible seal of said first pressable chamber is configured to be broken by the carrier.

According to another embodiment the invention provides a disposable cartridge, wherein the first frangible seal is configured to be broken by the carrier.

According to another embodiment the invention provides a disposable cartridge, wherein the succeeding frangible seal if configured to be broken by pressure.

According to another embodiment the invention provides a disposable cartridge, wherein in each one of said one or more parallel preparation units the last chamber is coupled to the second opening via a second channel, the second channel is sealable.

According to another embodiment the invention provides a disposable cartridge, wherein at least one of said one or more parallel preparation units includes two or more pressable chambers connected in series via one or more connecting channels, at least one of said one or more connecting channels is sealable.

According to another embodiment the invention provides a disposable cartridge, wherein each one of said one or more parallel preparation units are configured for introducing a carrier usable to introduce the sample fluid directly into a space of said first chamber.

According to another embodiment the invention provides a disposable cartridge, wherein performing a reaction is mixing said input fluid with a substance.

According to another embodiment the invention provides a disposable cartridge, wherein the pressable chambers are configured for mixing by jet flow created by pressure applicable to one or more pressable portion of said pressable chamber.

According to another embodiment the invention provides a disposable cartridge, wherein one or more of the chambers of at least one of said one or more preparation units include interconnected compartments, at least one of said interconnected compartments includes a pressable portion.

According to another embodiment the invention provides a disposable cartridge, wherein each compartment includes a pressable portion.

It is an additional object of the invention to provide an analyzing compartment for obtaining derivatives of a sample fluid and for presenting said derivatives in a way allowing analysis for the purpose of obtaining parameters of said fluid, the analyzing compartment comprising:
 at least one analysis unit, each analysis unit comprising:
  a hollow member configured for obtaining one or more of said derivatives and for presenting said derivatives in a way allowing analysis.

According to one embodiment the invention provides an analyzing compartment wherein the hollow member of one or more of said at least one analysis units being configured to obtain a first derivative of said derivatives for presenting prior to obtaining a second derivative of said derivatives for presenting.

According to another embodiment the invention provides an analyzing compartment wherein the at least one analysis unit comprises at least two analysis units and wherein said at least two analysis units are coupled in parallel and configured for presenting a derivative of said sample fluid in a way allowing to perform in parallel two types of analysis.

According to another embodiment the invention provides an analyzing compartment, wherein the hollow member of one or more of said at least one analysis unit is a chamber and wherein the one or more of said at least one analysis unit further comprising:
 a small cross sectioned channel coupled to said chamber, the small cross sectioned channel is configured for decelerating flow of a derivative of said sample fluid in the chamber.

According to another embodiment the invention provides a analyzing compartment, wherein an inner surface of the chamber of the one or more of said at least one analysis unit has projections coatable with an agent, and wherein the projections are configured to enlarge a contact area between said agent and said derivative f the sample fluid. It is yet another object of the invention to provide a disposable cartridge for obtaining a sample fluid containing cells and for preparing the sample fluid for analysis, the cartridge comprising:
 a series of at least two connected chambers, amongst said at least two chambers are a first chamber and a last chamber, each chamber in said series is enclosed between frangible seals and is configured to perform a procedure whose input is a first derivative of the sample fluid and whose output is a second derivative of said sample fluid;
 wherein the chambers in said series are configured for performing consecutive procedures,
 wherein the first derivative obtainable by the first chamber is the sample fluid; the first derivative obtainable by each one of all chambers apart of said first chamber is the second derivative respective of the preceding chamber in the series.

According to one embodiment the invention provides a disposable cartridge, wherein the seals comprising:
 a preceding seal configured for sealing a respective chamber prior to obtaining the first derivative; and
 a succeeding seal configured to be breached for releasing the second derivative from the respective chamber.

According to another embodiment the invention provides a disposable cartridge, wherein the preceding seal is a frangible seal.

According to another embodiment the invention provides a disposable cartridge, wherein the preceding seal is a re-sealable seal.

According to another embodiment the invention provides a disposable cartridge, wherein the succeeding seal is a frangible seal.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 6A and 6B depict another alternative preceding seal, according to certain embodiments of the invention;

DETAILED DESCRIPTION OF EXEMPLARY EMBODIMENTS

Figure 1:
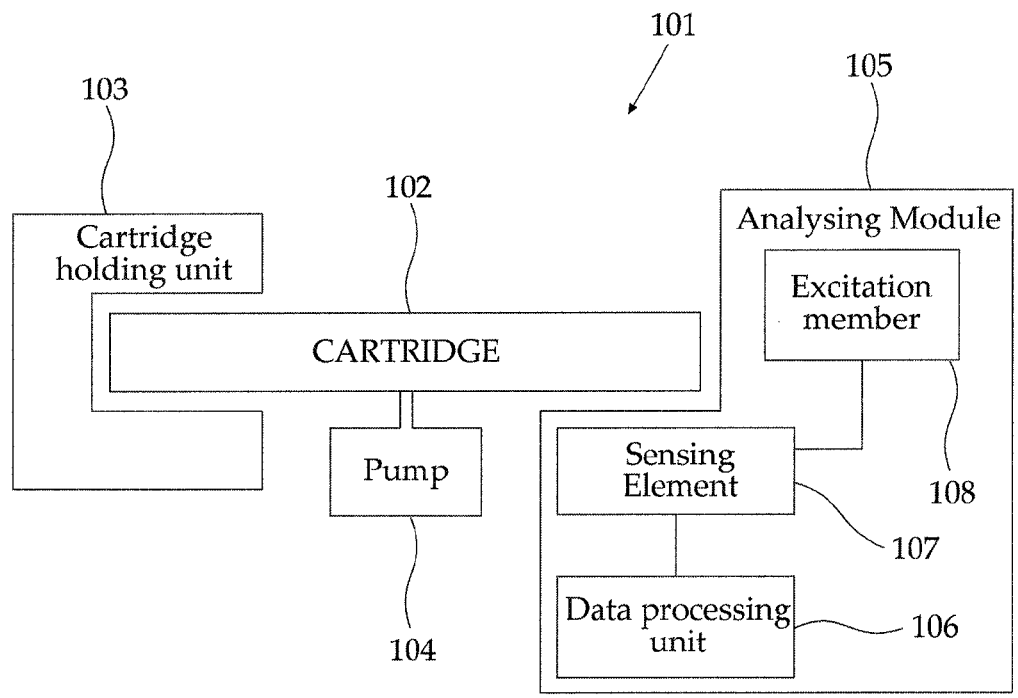
FIG. 1 schematically illustrates a system for analysis of a sample fluid using the cartridge, according to certain embodiments of the invention.

In the following description components that are common to more than one figure will be referenced by the same reference numerals.

In addition, unless specifically noted, embodiments described or referenced in the present description can be additional and/or alternative to any other embodiment described or referenced therein.

The object of this invention is to provide a cartridge for preparing a sample fluid containing cells for analysis. The sample fluid may be a body fluid, for example: blood, cerebrospinal fluid (CSF), pericardial fluid, pleural fluid, or any other fluid that may contain cells. Cells may be any type of prokaryotic cells, for example bacteria; eukaryotic cells, for example red blood cells; white blood cells (Leukocytes); epithelial cells; circulating tumor cells; cellular fragments, for example platelets; or others.

For the purpose of explaining the invention and due to consideration of simplicity, a cartridge for preparing blood sample for optical analysis resulting in obtaining a Complete Blood Count (CBC) is referenced throughout the description of the present invention. However, it should be appreciated that the invention is not limited to CBC. Disposable cartridges in accordance with the invention may be used for multiple applications where analysis of cells is desired, such as HIV monitoring (such as using CD4/CD8 ratio), detection of f-hemoglobin, Malaria antigen or other blood parasites, Paroxysmal Nocturnal Hemoglobinuria (PNH), diagnosis of Celiac disease using Intestinal Endomysial Autoantibodies (EmA), Alzheimer's disease, or any other application for which cell-based diagnosis is relevant.

FIG. 1 schematically illustrates a system 101 for analysis of a sample fluid using a cartridge 102, according to certain embodiments of the invention. For example, the system 101 may be usable as a Point of Care Testing (POCT) system which enables quick obtaining of laboratory results in a doctor's office. The system 101 comprises a cartridge holding unit 103, a pump 104, and an analyzing module 105 comprising a data processing unit 106. The analyzing module 105 may be configured to perform an analysis, e.g., optical analysis and/or electrical impedance analysis etc. Accordingly, the module may comprise a suitable sensing element 107 configured for detecting and measuring parameters used for analysis. For example, optical sensor (such as a CCD, CMOS or photo-multiplier) can be used in an analysis module configured for optical analysis. The module may also comprise an excitation member 108, such as a light source for emitting light of a pre-determined wave length suitable for the required type of analysis of the sample fluid. The excitation member 108 is possibly coupled to the sensor 107, e.g., in order to synchronize operations thereof. Also coupled to the sensor 107 is the data processing unit 106, that serves for processing and storing data acquired by a analysis module. The pump 104 serves for generating a pressure gradient, such as vacuum, that drives a flow of a sample fluid inside the cartridge.

In certain embodiments of the invention the system is configured for performing a complete blood count. In these embodiments the sensor 107 may be a camera which takes images of cells flowing inside the cartridge (as explained below with reference to the following figures). Acquired images are then processed by the data processing unit using suitable software and/or hardware in order to determine number of cells corresponding to each blood cell type (e.g., neutrophils, lymphocytes, erythrocytes, etc.) present in an analyzed blood sample.

Figure 2:
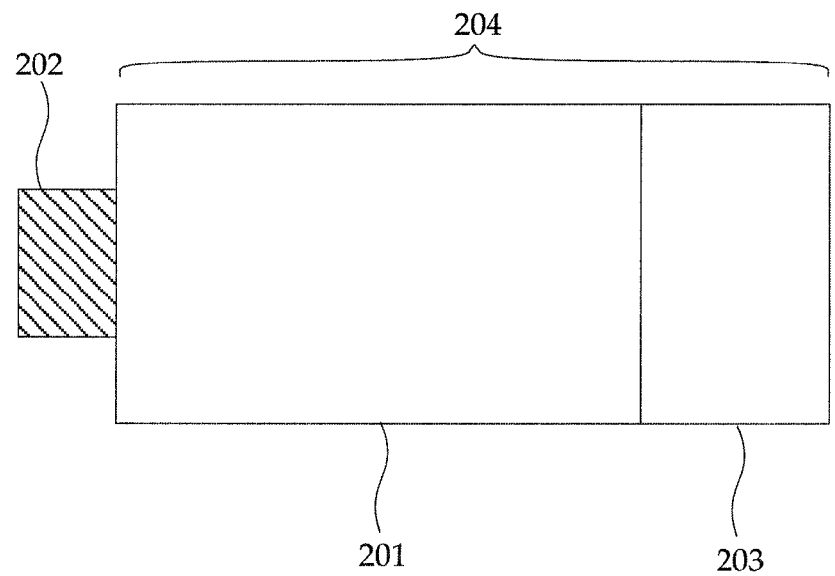
FIG. 2 schematically illustrates a cartridge already containing the body fluid as inserted into cartridge holding unit, according to certain embodiments of the invention.

FIG. 2 schematically illustrates a cartridge 201 according to certain embodiments of the invention. A sampler 202, serving for the introduction of a sample fluid into the cartridge is inserted into the cartridge 201 from one side. An analyzing compartment 203 is coupled to the cartridge 201 from the other side. While the preparation of the sample fluid for analysis is performed by the cartridge, presenting of the prepared sample fluid in a way allowing its analysis by the system 101 is performed by the analyzing compartment.

In a described embodiment the cartridge and the analyzing compartment are coupled. The cartridge and the analyzing compartment may be manufactured together and coupled during, or immediately after manufacturing, or they may be manufactured separately and become coupled prior to marketing the cartridge to its end user or even just prior to usage thereof, possibly even by a person performing the test or automatically inside system 101.

Although in FIG. 2 the cartridge and the analyzing compartment appear to be two separate compartments coupled together, this is non-limiting, and in other embodiments the analyzing compartment may comprise an integrative part of a cartridge. Furthermore, while in the present embodiment the analyzing compartment 203 appears as coupled to the cartridge, i.e., it is not an part thereof, in certain embodiments the analyzing compartment 203 may be considered as part of the cartridge while 201 relates to a "preparation compartment". That is, a cartridge 204 according to such embodiments may be composed of a preparation compartment 201 and an analyzing compartment 203. The cartridge 204 may also, according to certain embodiments, comprise a preparation compartment 201, and be coupleable to an analysis compartment. Hereinafter, due to simplicity considerations, the description refers to cartridge 201. However, it should be considered that although not specifically written, reference is made, mutatis mutandis, to cartridge 204 as well.

While in the embodiment illustrated in FIG. 2 the sampler 202 and the analyzing compartment 203 appear to be on both sides of the cartridge, this is non-limiting as well. According to other embodiments the sampler and the analyzing compartment may be positioned, with reference to the cartridge 201, in any way applicable to the case. For example, the analyzing compartment 203 may be positioned above or below the cartridge 201, on its side, on the side where the sampler 202 is positioned, or even in a gap, or a window, inside the cartridge.

Relating to the sampler 202, it is described below, with reference to FIG. 14. Yet, it should be mentioned here that the sampler is not a direct part of the cartridge 201 (or 204). It is a separate member having a carrier for holding the sample fluid, while the carrier can be, for example, a capillary. According to certain embodiments, the system 101 automatically couples the sampler 201 to the cartridge 201 or 204 in order to introduce the sample fluid thereto.

According to certain embodiments, the sampler may be considered as part of the cartridge, e.g., by coupling the sampler to the cartridge using any available mean such as a coupling-strip. Such a coupled sampler may be detached from the carrier (the capillary) in order to prevent it from breaking. Alternatively, it is possible to consider the sampler as part of the cartridge further to insertion of the carrier thereto.

Figure 3:
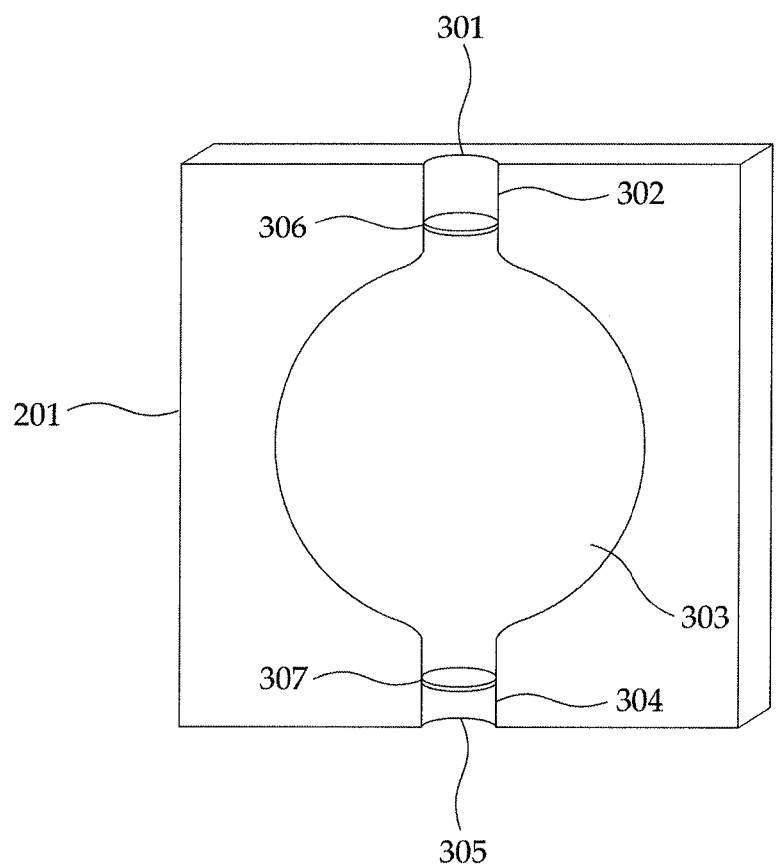
FIG. 3 provides a detailed illustration of a cartridge, according to a certain embodiments of the invention.

FIG. 3 provides a detailed illustration of a cartridge, according to certain embodiments of the invention. In the cartridge 201, a first opening 301, located in one of the sides thereof, is configured for receiving the carrier carrying a sample fluid. A first channel 302 is coupled to the first opening 301 and to a chamber 303. The chamber 303 is configured to receive the sample fluid and to perform a procedure affecting it, thereby forming an output fluid. Then, the chamber is configured to release the output fluid into the second channel 304, and therefrom out of the cartridge via a second opening 305. A preceding seal 306, configured to prevent flow from the chamber via the first opening is coupled to the first channel 302 while a succeeding seal 307, configured to prevent flow from the chamber via the second opening is coupled to the second channel 304.

It was previously explained that the term "output fluid" is used for referring to the fluid being the result of the procedure affecting the sample fluid, wherein the output fluid is further conveyed from the chamber. Hence, analogously, the fluid entering the chamber, prior to affecting the procedure, is referred to as "input fluid". It can be then observed that the input fluid of a chamber is the sample fluid introduced thereto.

In FIG. 3 the first and second openings are illustrated when they are positioned opposite one to the other. It should be appreciated though that this is non-limiting as the two openings may be perpendicularly positioned, for example. Any other relative position of the opening is allowed, with the necessary modification, including also positioning the two openings in the same side of the cartridge.

The procedure affecting a sample fluid, performed inside a chamber, such as chamber 303, may be any procedure resulting with a change of a physical or a chemical state of the sample fluid or of the cells contained within the sample fluid. Examples of possible procedures are heating, mixing, diluting, staining, permeabelization, lysis, etc. Some of the procedures will be described below with reference to the following figures.

In certain embodiments of the invention the chamber 303 is pre-loaded with a substance. The pre-loaded substance may be a liquid substance, a solid substance or a combination thereof. The substance may consist of a single reagent or of several different reagents. An example of a liquid substance consisting of several reagents is PBS (Phosphate Buffered Saline), while examples of solid substances are lyophilized antibodies, different kind of powdered stains dissolvable, e.g., in water or in ethanol, coated beads, etc. A substance may be lying free on the bottom of the chamber or may be attached to the inner surface of the chamber. Alternatively, a substance may be attached to a filling, such as sponge or microfibers, filling the space of the chamber, enlarging the surface area exposed to the sample fluid.

Furthermore, some possible procedures, such as heating, do not require having a pre-loaded substance in the chamber. Therefore, in certain embodiments the chamber is not pre-loaded with a substance, while it is possible that the chamber holds instead (or in addition to a pre-loaded substance) some sort of mechanism, such as a heating mechanism or part thereof. In addition, understanding that pre-loading the substance may be performed while manufacturing the cartridge or any time prior to the introduction of the sample fluid, it can be appreciated that according to alternative embodiments, the substance may be introduced into the chamber together with or after introducing the sample fluid. In other cases, wherein the substance is composed of a combination of constituents or wherein the substance is the outcome of a chemical reaction between more than one constituents, it is possible that at least one constituent is pre-loaded while at least one other constituent is introduced with or after introduction of the sample fluid.

In case the chamber 303 is loaded with a substance, whether pre-loaded or loaded with/after introduction of the sample fluid, the procedure affecting the sample fluid may be mixing of the sample fluid with the substance. Normally with reference to such a procedure, the sample fluid and the substance must be mixed thoroughly as lack of homogeneity will adversely affect subsequent analysis. According to certain embodiments of the invention, in order to enable mixing, at least part (a portion) of the surface of the chamber, comprises a pressable portion made of an elastic polymer, for example polyurethane or silicone, or of a different elastic material. Due to deformation (such as constriction) of the chamber, affected by pressing and/or releasing the pressable portion, fluid contained within the chamber will form a jet flow inside the chamber, a form of flow that enhances mixing. Hence, according to embodiments of the invention, it is possible to achieve mixing by alternatively pressing and releasing the pressable portion of the chamber. When the pressable portion is pressed the fluid flows away and when it is released it flows back, that is, the fluid flows back and forth.

In certain embodiments of the invention a pressable portion constitutes a part of a chamber's surface, for example, an upper surface of a chamber or a certain percentage of its surface, while in different embodiments of the invention the entire chamber is pressable. That is, 100% of the chamber surface are also considered as a portion thereof.

Apart of or in addition to mixing, procedures affecting the sample fluid performed in the chamber may be reactions that may occur between the substance and the sample fluid. The reaction may be a chemical reaction, for example oxidation/reduction, or a biochemical reaction such as binding antibodies to ligands. The procedure may lead to changes in physical and/or chemical states of the sample fluid or of cells contained within the sample fluid. For example, it may affect changes in viscoelastic properties or in pH of the sample fluid; Concentration of cells contained in a sample fluid may decrease due to dilution; A cellular membrane may become permeable enabling binding of coloring agents or antibodies contained within the substance to cellular components, such as cytoplasmic granules; An oxidation or reduction of different cellular components may happen, such as oxidation of hemoglobin contained in the red blood cells into methemoglobin; etc.

After the procedure has been completed, the resulting output fluid is released from the chamber. The releasing may be affected by positive pressure, "pushing" the fluid out of the chamber, for example if fluid is being pushed out of the chamber by pressing, or it may be affected by negative pressure, for example if fluid is driven out of the chamber by physical forces the "pull" it out, such as gravitational force or due to application of external forces such as vacuum. For example, in certain embodiments of the invention the flow of the output fluid from the chamber via the second opening into the analyzing compartment is driven by a suction force generated by the vacuum pump 104 coupled to the analyzing compartment, as will be described further with reference to FIG. 10.

It was mentioned before that the chamber is enclosed between two seals, wherein the preceding seal 306 prevents fluid from flowing out of the chamber via the first opening 301 while the succeeding seal 307 prevents fluid from flowing out of the chamber via the second opening. It should be appreciated that prior to introduction of the sample fluid the two seals 306 and 307 should prevent release of the substance from the chamber; then they should prevent release of the substance and/or the sample fluid during the procedure; and they should also prevent unintentional release of the output fluid prior to the intentional release thereof.

Due to simplicity considerations attention is drawn first to the succeeding seal 307. It should be appreciated that breaking, or breaching the succeeding seal allows output fluid flowing out of the chamber towards the second opening. According to certain embodiments, after breaching the seal it is not required anymore and therefore it may be left open. Thus, the second seal 307 constitutes a "frangible seal". It is possible to form the seal, e.g., of adhesive configured to be to be broken by application of pressure exceeding a certain threshold. Applying excessive pressure on the pressable part of a chamber, whose outcome is super-threshold pressure at the position of the seal, breaches the succeeding seal. The output fluid is then released to flow through the second channel via the second opening into the analyzing compartment. In other words, the output flow is conveyed to the analyzing compartment via the second channel and via the second opening.

It is noted that mixing of the sample fluid with the substance by intermittently pressing the pressable portion of the chamber does not result in super-threshold pressure at the position of the seal, which therefore remains intact. Alternatively or additionally, it is possible to protect the seal from being affected be super-threshold pressure by applying pressure on the channel between the chamber and the seal, hence obtaining a physical obstacle preventing pressure arising in the chamber to reach the seal. According to a different alternative it is possible to apply the pressure further to the seal. According to this embodiment supper-threshold pressure may reach the seal and breach it, however the physical obstacle affected on the channel will prevent fluid from flowing, until the obstacle is removed. It is further clarified, with reference to the two last alternative embodiments, that the pressure applied on the channel in these cases is impermanent.

Further to understanding how breaching of the succeeding seal can happen, attention is now drawn to the preceding seal 306. This seal has two different roles. The first role is preventing release of the substance from the chamber prior to the introduction of the sample fluid. However, when introducing the sample fluid, the preceding seal must be broken, in order to allow such introduction. Yet, it was previously explained that in order to allow mixing using pressure affected to the pressable portion of the chamber, the chamber must be sealed from both sides. Therefore, the preceding seal has a second role: unlike the succeeding seal, the preceding seal must be re-sealed after introduction of the sample fluid, in order to allow mixing and in order to prevent unintentional release of the output fluid from the chamber.

It was previously explained that the sample fluid may be introduced via the first opening using a carrier. In light of the latter explanation relating to re-sealing, it should be appreciated that in those embodiments wherein the carrier is left in the cartridge further to the sample fluid introduction, re-sealing should seal passage of fluid via the gap existing between the carrier and the first channel's internal surface.

Figure 4B:
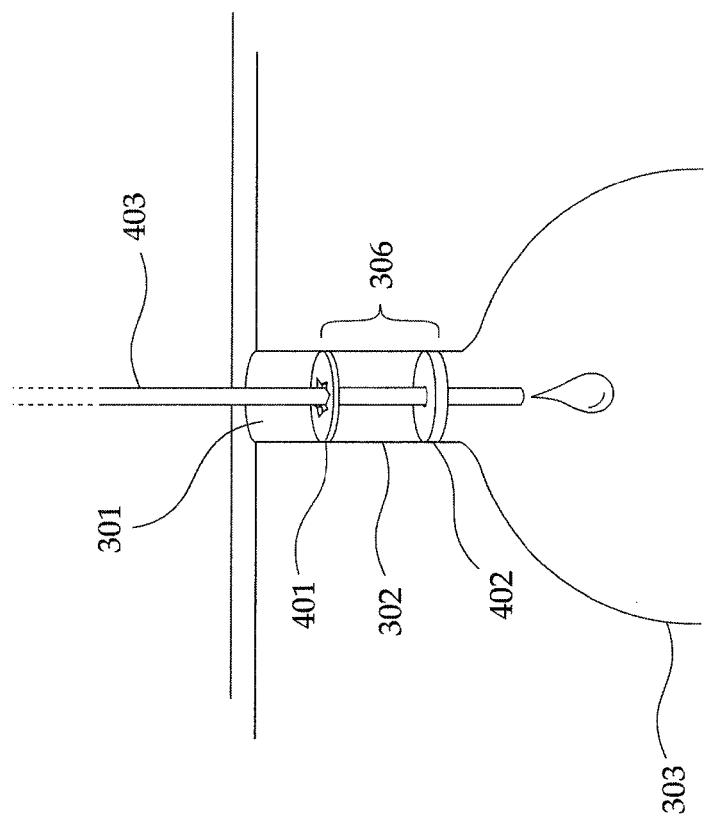
FIGS. 4A and 4B depict a preceding seal, according to certain embodiments of the invention.
Figure 4A:
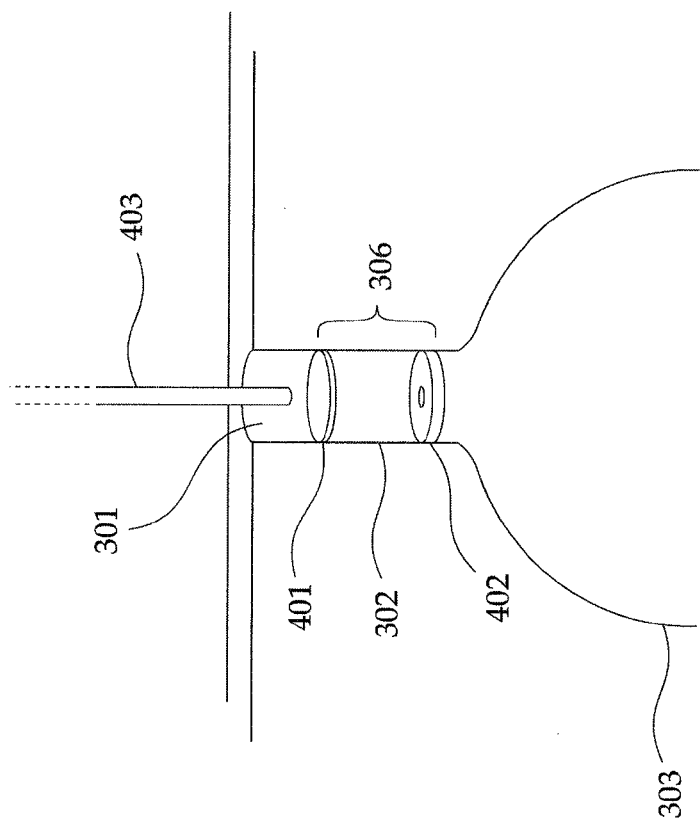

FIGS. 4A and 4B depict a preceding seal 306, according to certain embodiments of the invention. The embodiments illustrated by the figures are adapted for a carrier that remains inside the first channel further to the delivery, or introduction of the sample fluid.

In accordance with the illustrated embodiments, the depicted preceding seal 306 is comprised of two separate seals, namely, a first seal 401 and a second seal 402. FIG. 4A depicts the preceding seal prior to introduction of the sample fluid using a carrier 403, while FIG. 4B depicts the seal when the carrier is inserted, penetrating the preceding seal 306.

The first seal 401 is configured to prevent flow from the chamber via the first opening prior to introduction of the sample fluid (the first role mentioned above). Hence, similar to the succeeding seal, the first seal 401 may be a frangible seal, formed of adhesive or a plug. Upon insertion of the carrier 403 into the chamber via the first opening, the carrier 403 breaks seal 401, as illustrated in FIG. 4B.

The second seal 402 is in charge of re-sealing the chamber further to the insertion of the carrier (the second role mentioned above). The second seal is configured to prevent the leakage through the interface between the carrier, more accurately, the outer surface of the carrier, and the inner surface of the channel. According to certain embodiments, the seal is comprised of a flexible ring mounted inside the channel (an o-ring). The inner diameter of the ring is smaller than the diameter of the carrier, hence, the ring allows the carrier to pass through, while closing tight around to prevent leakage. According to alternative embodiments the first seal 401 and the second seal 402 may be swapped, that is, seal 402 may appear prior to the first seal 401.

Prior to continuing to additional and/or alternative embodiments, it is noted that the carrier may be hollow inside. Hence, after the insertion thereof flow, or leakage out of the chamber may occur also through the inner space of the carrier. According to certain embodiments, illustrated and described, e.g., with reference to FIG. 14 below, this leakage is prevented by a hydrophobic membrane located inside the carrier.

Figure 5A:
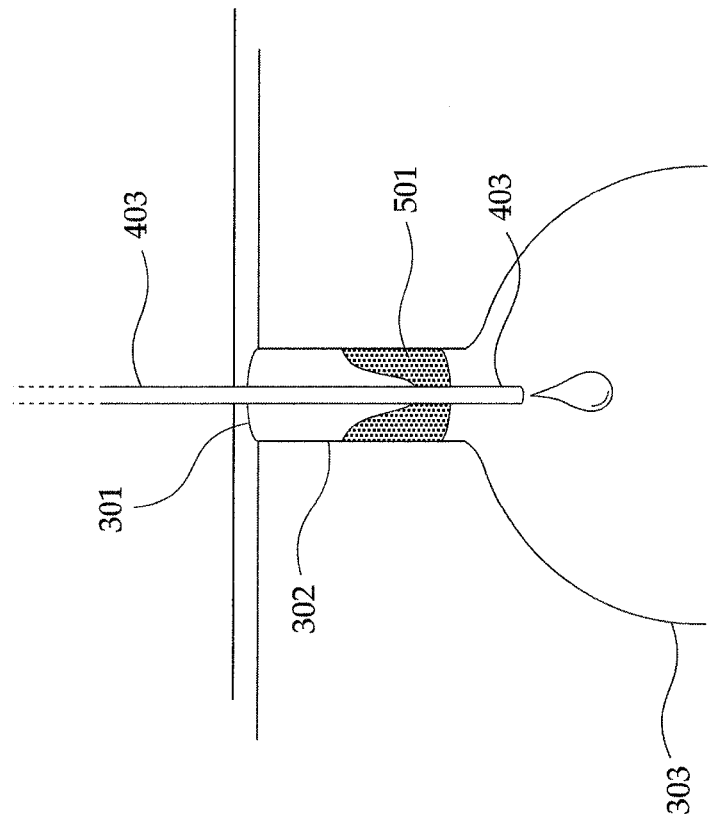
FIGS. 5A and 5B depict preceding seal alternative to the seal illustrated in FIGS. 4A and 4B, according to certain embodiments of the invention.
Figure 5B:
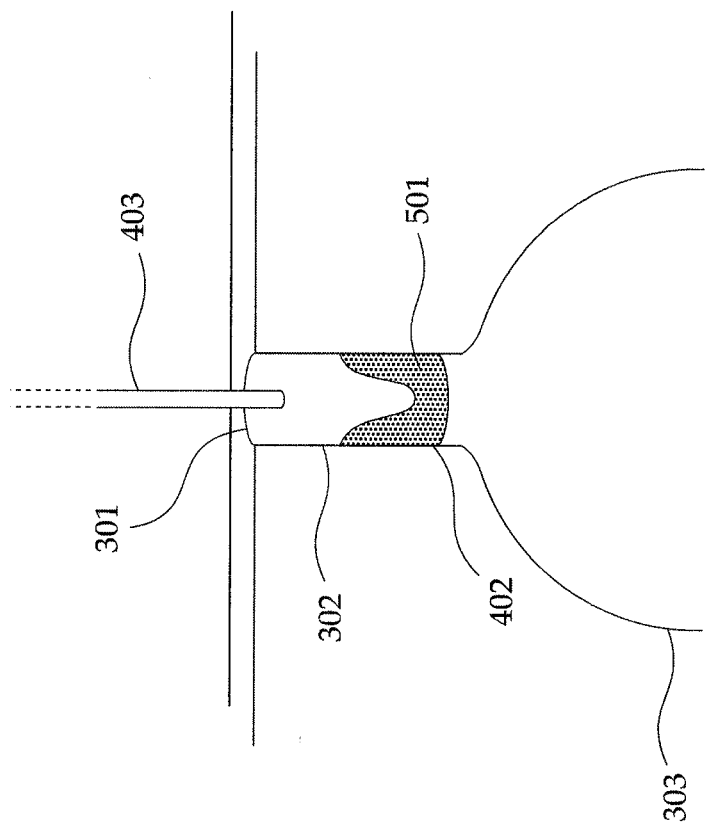

FIGS. 5A and 5B depict a preceding seal, alternative to the seal illustrated in FIGS. 4A and 4B, according to certain embodiments of the invention. Unlike the embodiment of FIGS. 4A and 4B wherein the seal 306 is comprised of two seals (namely, these are the first 401 and second 402 seals), the seal in the present figure is comprised of a single member whose functionality is similar to the functionality of seals 401 and 402 when combined. In FIG. 5A, a stopper 501 with centering shoulders is molded inside the first channel 302. Stopper 501 prevents flow from the chamber via the first opening 301, prior to the introduction of the sample fluid. Upon insertion of a carrier 403, as illustrated by FIG. 5B, the center of the stopper 501 is breached, while the shoulders of the stopper block the interface between the outer surface of the carrier and the inner surface of the channel, preventing leakage further to the sample fluid introduction. According to certain embodiments stopper 501, that forms preceding seal 306, may be mad of a soft adhesive elastomer.

FIGS. 6A and 6B depict another alternative preceding seal, according to certain embodiments of the invention. Similar to seal 501 of FIGS. 5A and 5B, the present embodiments' seal 601 also describes a single seal combining the functionality of the first and second seals (404 and 402) illustrated in FIGS. 4A and 4B. Unlike the stopper 501 (of FIG. 5) that is configured for being breached by the carrier, according to the present embodiments the preceding seal is an enjected eyelet 601 with an integrated plug 602, configured for being displaced, pushed by the carrier. The eyelet 601 and the plug 602 may comprise different units or may belong to the same unit, i.e., they me be coupled or not. As illustrated in FIG. 6A, the plug is coupled to the eyelet and hence they form the same unit. However, this is non-mandatory. The plug may be coupled, e.g., to the chamber or to the channel, or it may have no coupling mechanism where applicable.

According to FIG. 6A, prior to the introduction of the sample fluid, the plug is closed, hence it prevents flow from the chamber via the first opening. FIG. 6B illustrates introduction of sample fluid to the chamber while using a carrier such as a capillary. Upon insertion of the carrier, the plug is pushed inwards, thus opening the channel, however the eyelet 601 seals the interface between the outer surface of the carrier and the inner surface of the channel, preventing leakage thereby.

Further to presenting several embodiments for applying a preceding seal, it should be appreciated that there may exist other embodiments, wherein following the introduction, or delivery of a sample fluid into the chamber, the carrier is withdrawn from the first channel. An example for such a carrier is a needle attached to a syringe usable to deliver the sample fluid into the first chamber. In such cases the preceding seal has to re-seal the opening left after the carried is withdrawn. An example for such a seal is a known per se septum.

Before describing the invention further, a summary of a process of preparation of a sample fluid for analysis, according to certain embodiments of the invention is presented. A carrier 403 of a sample fluid is inserted via the first opening 301 into the first channel 302. The carrier breaches the preceding seal 306 coupled to the first channel and delivers the sample fluid into the chamber 303. Inside the chamber a procedure is affected to the sample fluid, such as mixing the delivered sample fluid with a substance pre-loaded to the chamber, thus obtaining an output fluid. Mixing is enabled by applying an intermittent pressure on a pressable portion of the chamber. Upon completion of the procedure, the succeeding seal 307 becomes broken by pressing the chamber in a way generating a super-threshold pressure at the position of the succeeding seal, resulting in a release of the obtained output fluid from the chamber. The released output fluid then flows via the second channel 304 and the second opening 305 into the analyzing compartment 203, wherein it is subjected to analysis.

Figure 7:
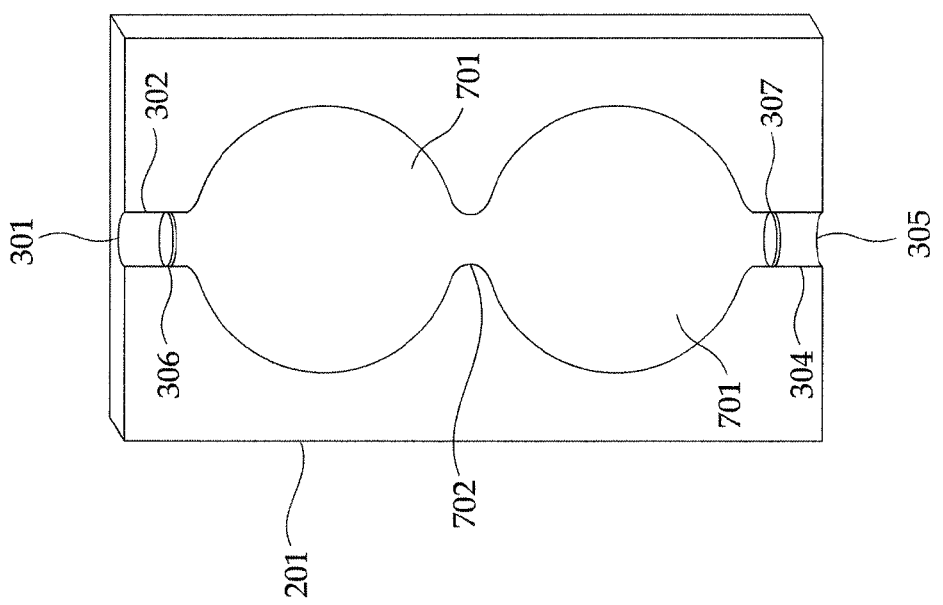
FIG. 7 presents a cartridge comprising a chamber containing two compartments, according to certain embodiments of the invention.

FIG. 7 presents a cartridge comprising a chamber (e.g., a mixing chamber) containing two compartments, according to certain embodiments of the invention. The two compartments 701, which may be pre-loaded with a substance, are interconnected by a narrowing 702. The first compartment is coupled to the first opening 301 via a first channel 302, while the second compartment is coupled to the second opening 305 via a second channel 304. At least one, and possibly two of the compartments includes a pressable portion.

In case that both compartments have pressable portions, it is possible to achieve mixing by alternating pressure applied to the two pressable portions (each compartment in a time). The narrowing 702 between the compartments 701 causes jet flow, hence enhancing mixing. Breaking the succeeding seal 308 may be caused, e.g., by simultaneously pressing both compartments and/or by applying stronger pressure than the pressure applied for mixing.

In case that there is only one pressable portion, on one of the compartments, it is possible to achieve mixing by intermittently pressing this portion. Breaking the succeeding seal 308 may be caused by applying excessive pressure on the pressable portion.

In the description of the latter embodiment it was written that the substance is pre-loaded into the two compartments. Prior to continuing to describe additional and alternative embodiments, it should be noted that the substance may be loaded into only one compartment, if applicable.

In addition, instead of having two compartments having the form illustrated in FIG. 7, it is possible to have alternative embodiments, having other forms. For example, the chamber may appear from the outside as the chamber illustrated in FIG. 3, having a partitioning member inside. An opening or even a valve in the partitioning member may function as the narrowing in FIG. 7.

In the embodiments described so far the cartridge comprised one chamber. However, the invention is not limited thereby, and, in different embodiments the cartridge may contain more than one chamber, wherein the chambers are connected in series. Hereinafter, one or more chambers enclosed between frangible seals and connected in series constitute a "preparation unit". Therefore the cartridge described, e.g., with respect of FIG. 3 can be defined as a cartridge comprising one preparation unit containing a single chamber. Similarly, the cartridge of FIG. 7 is also a cartridge comprising one preparation unit containing a single chamber.

Figure 8:
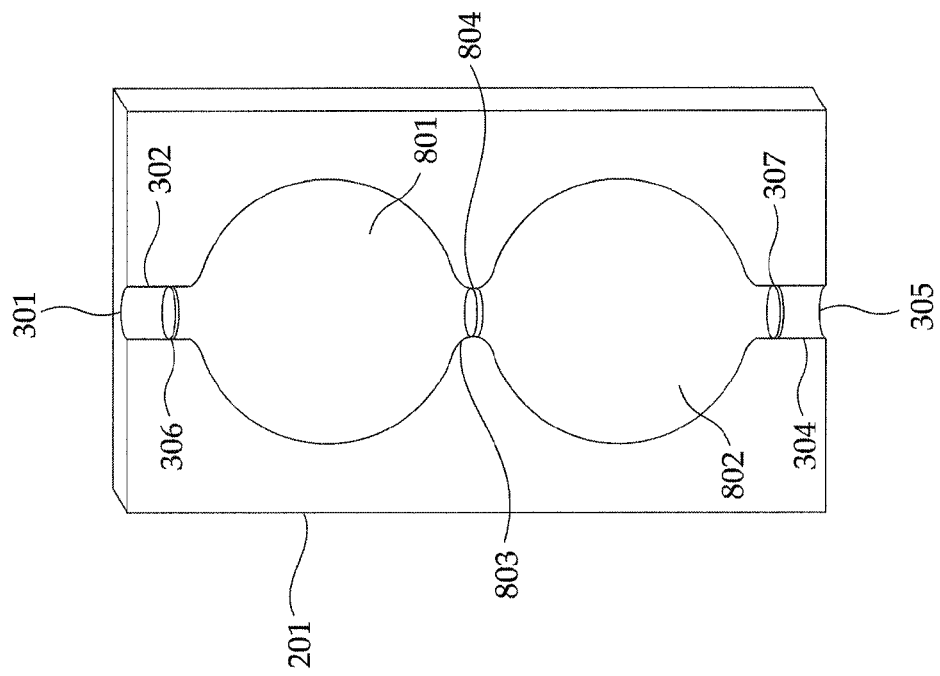
FIG. 8 presents a cartridge comprising a preparation unit composed of two chambers, according to certain embodiments of the invention.

FIG. 8 presents a cartridge comprising a preparation unit composed of two chambers, according to certain embodiments of the invention. A first chamber 801 (e.g., a first reagent chamber), coupled to a first opening 301, is a pressable chamber, while a last chamber 802 (e.g., a second reagent chamber), coupled to a second opening 305, might be either pressable or not pressable. The two chambers, are connected by a connecting channel 803 sealed by a seal 804. The two chambers are enclosed, each, between seals, whereas the first chamber 801, is preceded by a preceding seal 306 and the last chamber 802, is succeeded by a succeeding seal 307. Seal 804 is a succeeding seal with respect to chamber 801, while with respect to chamber 802 it is a preceding seal.

In the illustrated case, the first and the second openings of a preparation unit constitute respectively the first and the second openings of a cartridge. This however is non-limiting, and in different embodiments, for example in the embodiments described by FIG. 9 below, the first and the second openings of a preparation unit may be distinct from the first and the second openings of a cartridge.

While each chamber has a respective input fluid and a respective output fluid, the input fluid of the first chamber, introduced thereto via the first opening, is a sample fluid. Inside the first chamber a procedure affecting the fluid is performed. This procedure is referred to as a "first procedure". In case the procedure includes mixing, it is performed as described with reference to FIG. 3. By affecting appropriate pressure on seal 804 it may be breached (see FIG. 3 and the description relating thereto), resulting in release of the output fluid from the first chamber, conveying it to the last chamber. The output fluid of the first chamber becomes, therefore, an input fluid of a last chamber.

At this stage it should be considered that if seal 804 is a frangible seal, further to breaching it the path between the two chambers 801 and 802 is left open and flow is possible at both directions, that is from 801 to 802 and from 802 to 801. Hence, the two chambers form, in effect, two compartments of a single chamber. Therefore, in embodiments having a frangible seal in the connecting channel 803, further to breaching this seal the output fluid of the first chamber 801 can flow back and forth between the two former chambers, while being affected by the procedure of the last chamber. That is, the two chambers form two compartments of the last chamber. The description provided with reference to FIG. 7 may be applicable to this last chamber comprised of two compartments (801, 802).

Understanding this, it is noted that because 802 and 801 now effectively form a single chamber, the channel connecting this single chamber to the second opening, that is the second channel, may couple "compartment" 801 with the opening instead of "compartment" 802.

However, if seal 804 is re-sealable, further to conveying chamber 801's output fluid to chamber 802, the latter chamber can be re-sealed, therefore the description provided with reference to chamber 303 in FIG. 3 may be applicable thereto. An example of a re-sealable seal is a valve. Moreover, instead of using a sealable seal, certain embodiments may have a re-sealable connecting channel 803, while re-sealing may be performed, for example, by applying pressure to the connecting channel 803, hence obtaining a physical obstacle preventing fluid from flowing at this route.

Inside the last chamber a procedure, referred to as a "second procedure", is performed. By affecting appropriate pressure on the succeeding seal 307, it may be breached, thus resulting in release of the output fluid from the last chamber towards the second opening 305. The output fluid of the last chamber constitutes, therefore, an output fluid of a preparation unit. The output fluid of the preparation unit flows via the second opening 305 into the analyzing compartment 203, wherein it is subjected to analysis.

After describing the embodiments of FIG. 8 with reference to FIGS. 3 and 7, it should be appreciated that these embodiments are non-limiting as a preparation unit may be comprised of one, two, or more than two chambers. In general, a preparation unit may be comprised of one or more chambers connected in series, each chamber is enclosed between frangible seals. Each chamber is configured for receiving an input fluid, performing a procedure affecting the fluid thereby generating an output fluid, and releasing the output fluid. A first chamber of the one or more chambers is coupled to a first opening, while a last chamber is coupled to a second opening. A first chamber is a pressable chamber, whereas the preparation unit may include additional pressable chambers. The input fluid of the first chamber is a sample fluid while the input fluid of each one of the other chambers is the output fluid of the chamber preceding thereto. The output fluid of the last chamber comprises the output fluid of the preparation unit to be subjected to analysis.

It is noted that according to certain embodiments in a preparation unit including, e.g., two chambers, it is possible to apply pressure on the first chamber in order to breach the seal inbetween. Alternatively, the seal may be breached by applying pressure on the second chamber.

Further to understanding how the preparation of FIG. 8 operates, it should be appreciated that other embodiments may have preparation units with more than two chambers, wherein each chamber is enclosed between seals, namely a preceding seal and a succeeding seal. The preceding and/or the succeeding seals may be frangible or re-sealable. That is, according to certain embodiments of the invention, there may exist series of two or more chambers. Amongst the serialized chambers there are, at least, a first chamber and a last chamber, while the first chamber is coupled to the first opening (a sample fluid is introduced therethrough into the first chamber) via a first channel and the last chamber is coupled to the second opening via the second channel.

Each chamber in the series is configured to perform a procedure. Hence, if the first chamber obtains the sample fluid, it may be appreciated that the procedure respective of the first chamber affects this sample fluid, yielding a derivative of the sample fluid. The derivative manifests a change having occurred in a sample fluid or in cells contained within the sample fluid. The occurred change may be a chemical change, a biochemical change or a physical change. Examples of a chemical change are change in pH, oxidation/reduction of cellular components or hinging of chemical agents, such as dyes thereto; examples of a biochemical change is binding of antibodies to ligands; whereas examples of physical change are changes in viscoelastic properties, in temperature or in concentration of diluents. According to an alternative view, the sample fluid may be considered as a derivative of itself, i.e., a derivative of the sample fluid. Hence, the procedure obtains as input a derivative of the sample fluid, and yields an output which is a derivative of the derivative. In order to clarify this, the derivatives are given "names": the chamber obtains a first derivative of the sample fluid, while the procedure's output, and hence also the chamber's output, is a second derivative of the sample fluid.

Understanding how the first chamber operates, it should be appreciated that this is correct to all the other chambers in the series: each chamber obtains an input fluid which is a first derivative of the sample fluid, the first derivative is the input of the procedure operative with respect of the chamber. Then, the output of the procedure is a second derivative of the sample fluid, while this second derivative is also the output of the chamber.

Because the chambers are consecutive, so are the procedures: the procedure of a certain cell in the series yields a second derivative of the sample fluid, which is the output of the chamber. The consecutive chamber obtains the second derivative being output of the preceding chamber, while here (in the consecutive chamber) it is considered as a first derivative, being input to the consecutive chamber's procedure. The output of the consecutive chamber's procedure is a respective second derivative of the sample fluid. This second derivative is further conveyed to the coming chamber, a chain that lasts until the last chamber conveys its respective second derivative of the sample fluid towards the second opening.

An example for consecutive procedures is an immune-labeling of cells: labeling with a primary antibody is performed in a first chamber followed by a consecutive labeling with a secondary antibody, performed in a last chamber. Another example is differential staining of white blood cells of a blood sample, with two staining reagents, that must be separated during storage. Procedure of staining with a first reagent, performed in a first chamber, is followed by staining with a second reagent, performed in a consecutive, possibly last chamber.

It should be appreciated that in accordance with embodiments of the present invention the procedure is performed inside the chambers, wherein each chamber adds a stage in the preparation of the output fluid, all together resulting in a cumulative continuous process. This is unlike having the procedures performed in a dedicated chamber. Hence, efficient and complete mixing of the fluid and the reagents is affected.

Figure 9A:
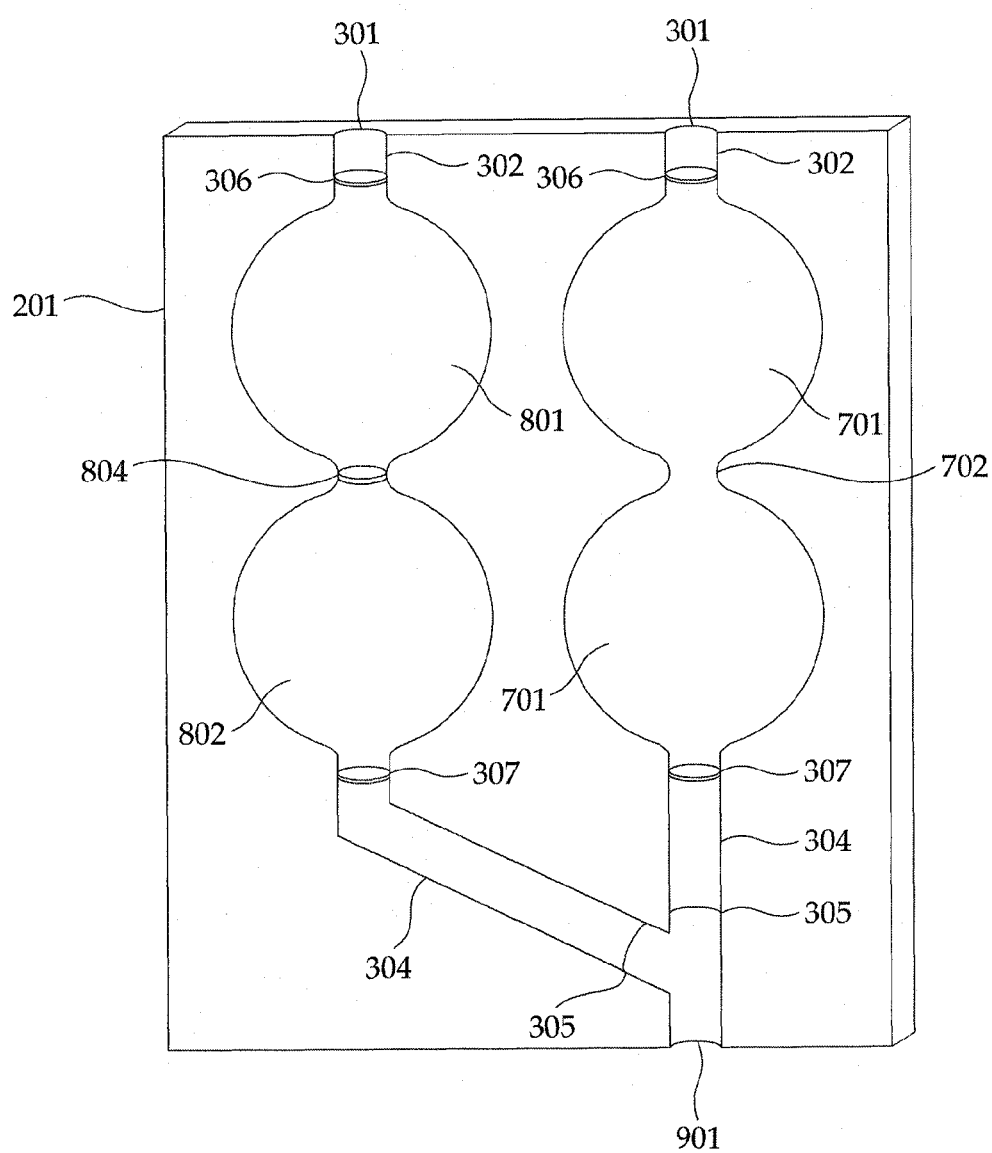
FIGS. 9A and 9B presents two configurations of a cartridge comprising more than one preparation unit, according to certain embodiments of the invention.
Figure 9B:
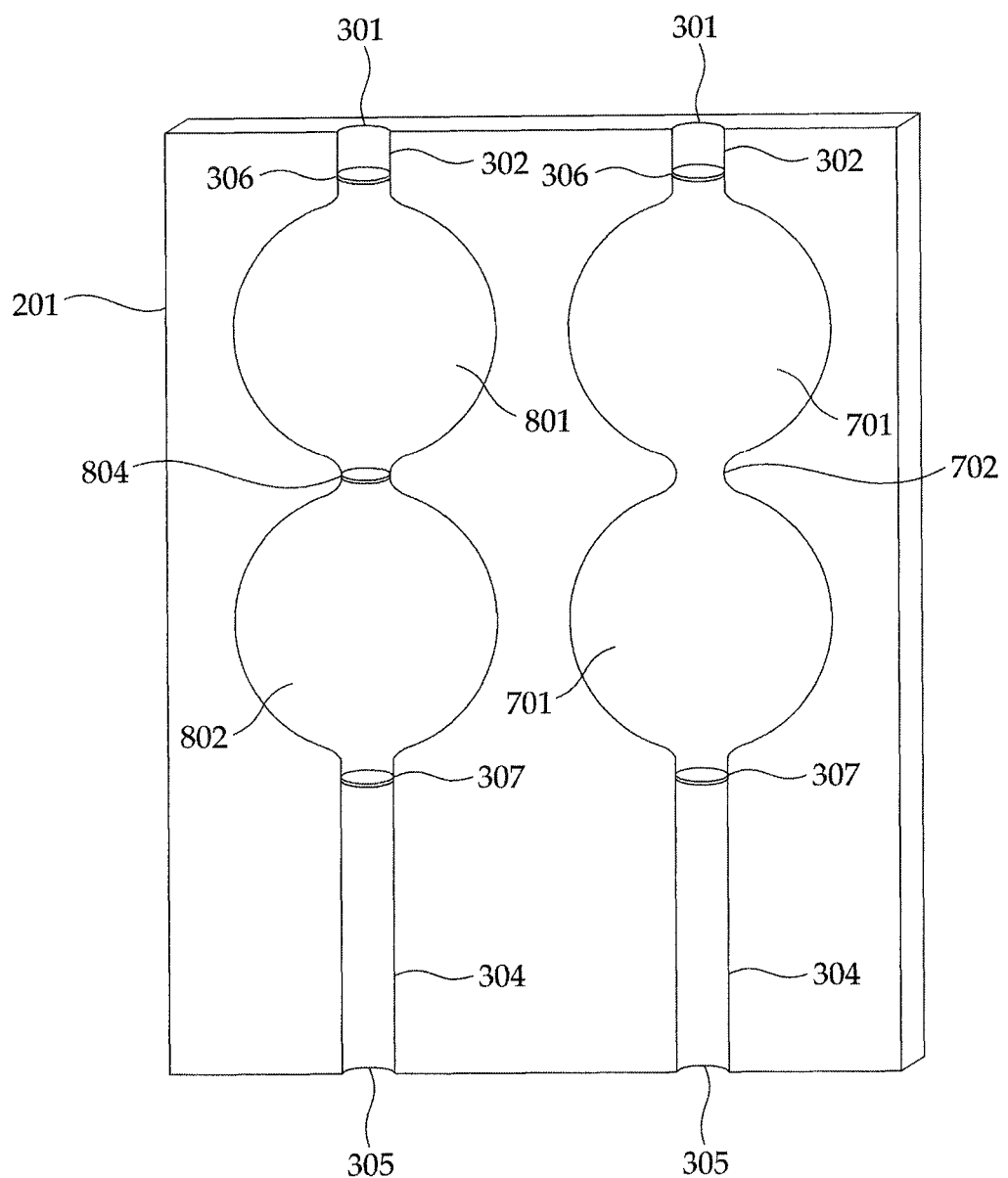

FIGS. 9A and 9B presents two configurations of a cartridge comprising two preparation units, according to certain embodiments of the invention. One of the preparation units comprises a single chamber containing two interconnected compartments 701. This preparation unit has been described above, with reference to FIG. 7. The other preparation unit comprises two chambers 801 and 802, connected by a channel 803 and sealed by a seal 804. This preparation unit has been described above, with reference to FIG. 8. Each preparation unit has a respective first opening 301 and a respective second opening 305. The first openings of both preparation units constitute the first openings of the cartridge.

The two configurations of the cartridge, depicted by FIGS. 9A and 9B, differ respective to number of the cartridge second openings present therein. The cartridge depicted at FIG. 9A has a single cartridge second opening 901 which is distinct from the second openings 305 of the preparation units. The cartridge depicted at FIG. 9B has two preparation unit's second openings 305, which, in this case, constitute also second openings of the cartridge.

In the described embodiments each preparation unit of a cartridge is configured for introduction of a sample fluid by a respective carrier. This however is not limiting, and in certain embodiments preparation units of a cartridge may be configured for introduction of sample fluid from a single carrier. The sample fluid may be introduced into the preparation units simultaneously or consequently, as will be explained further below with reference to FIG. 14.

The output fluid of each preparation unit may flow into the analyzing compartment at different timings and may be subjected to separate analysis, as will be explained further below with reference to FIGS. 13B and 13B.

Existence of two parallel preparation units enables performing two separate independent procedures affecting the sample fluid. For example, in certain embodiments of the invention, the cartridge is configured for performing a complete blood count. The cartridge comprises two parallel preparation units, whereas one preparation unit is configured for preparation of red blood cells for analysis, while the other preparation unit is configured for preparation of white blood cells for analysis (the abovementioned procedures will be explained in details below, with reference to FIGS. 13A and 13B).

Although the cartridges depicted by FIGS. 9A and 9B comprise two preparation units, this is not limiting. The number of preparation units constituting a cartridge, as well as the number of chambers constituting each preparation unit and the number of chambers containing more than one compartment may differ, as configuration of a cartridge is tailored for performance of desired procedures and/or for purpose of preparing the sample fluid for certain analysis procedures.

Figure 10:
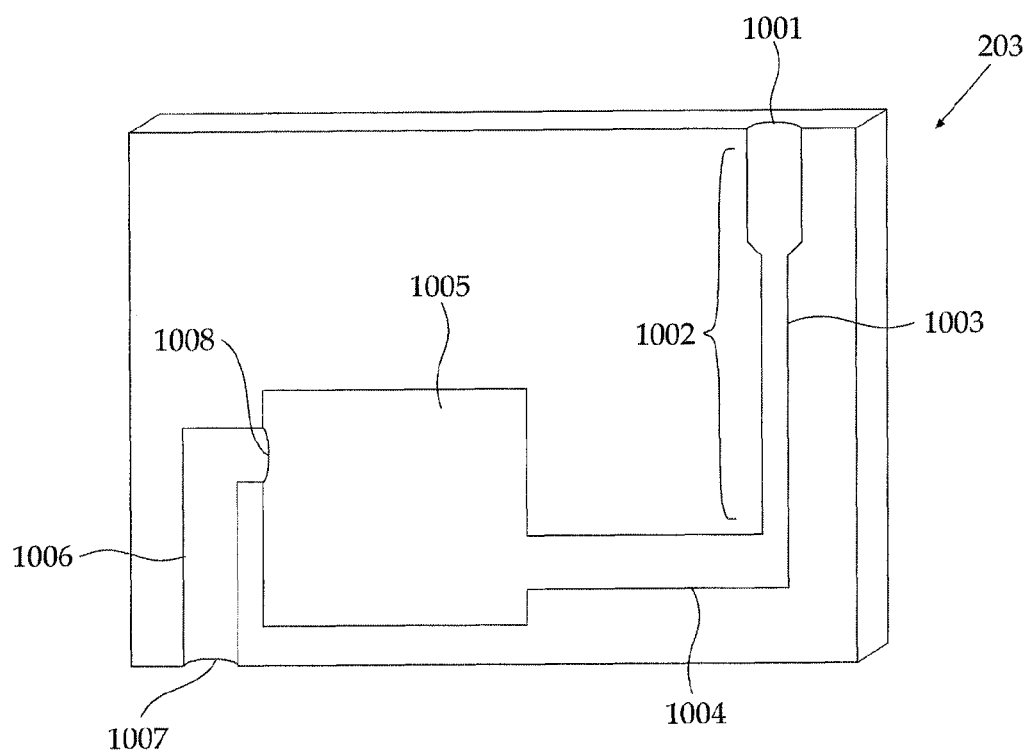
FIG. 10 schematically illustrates an analyzing compartment, according to certain embodiments of the invention.

FIG. 10 schematically illustrates an analyzing compartment, according to certain embodiments of the invention. The analyzing compartment comprises an analysis vessel 1002, configured for receiving the output fluid conveyed by preparation unit or units and for presenting it in a way allowing analysis, and from a third channel 1004, coupled to the analysis vessel and configured for emptying disposable output fluid therefrom. The analysis vessel and the third channel together comprise an analyzing unit. A waste container 1005, configured for storing disposed output fluid is coupled to the analysis unit via the third channel 1004. The waste container 1005 is also coupled to a vacuum pump 104 via a fourth channel 1006.

An output fluid flows from a preparation unit into the analyzing unit via a third opening 1001. Inside the analysis vessel 1002 the output fluid is presented to an analyzing system 101. After being subjected to analysis the output fluid is disposed via the third channel 1004 into the waste container 1005 and stored therein.

The flow of the output fluid inside the analyzing unit is driven by a suction force generated by the vacuum pump 104, which may be a part of the analyzing system 101. The vacuum pump is coupleable to the analyzing unit through a fourth opening in the analyzing compartment, connected via the fourth channel 1006 to the fifth opening 1008 in the waste container 1005. Although the suction force is applied to the waste container, the stored output fluid does not flow out therefrom, because the waste container should be designed as a liquids trap in any way known per se. In the figure the fifth opening 1008 is located above the level of the stored output fluid, hence schematically representing such a liquid trap.

In certain embodiments of the invention, illustrated by FIG. 10, an analysis vessel of the compartment is a microchannel 1003 configured to align cells contained in the output fluid into a single plane, allowing taking images of the flowing cells by a camera 107, or probing by a focused light beam/laser beam as done in a cytometer. The aligning of the cells may be performed by a method known as viscoelastic focusing. Viscoelastic focusing is described in PCT Publication No. WO2008/149365 entitled "Systems and Methods for Focusing Particles", while a microchannel configured for viscoelastic focusing is further described in PCT Publication WO2010/013238, entitled "Microfluidic System and Method for Manufacturing the Same". The aligned cells may then be optically analyzed, through a transparent or translucent surface of the microchannel.

Figure 11:
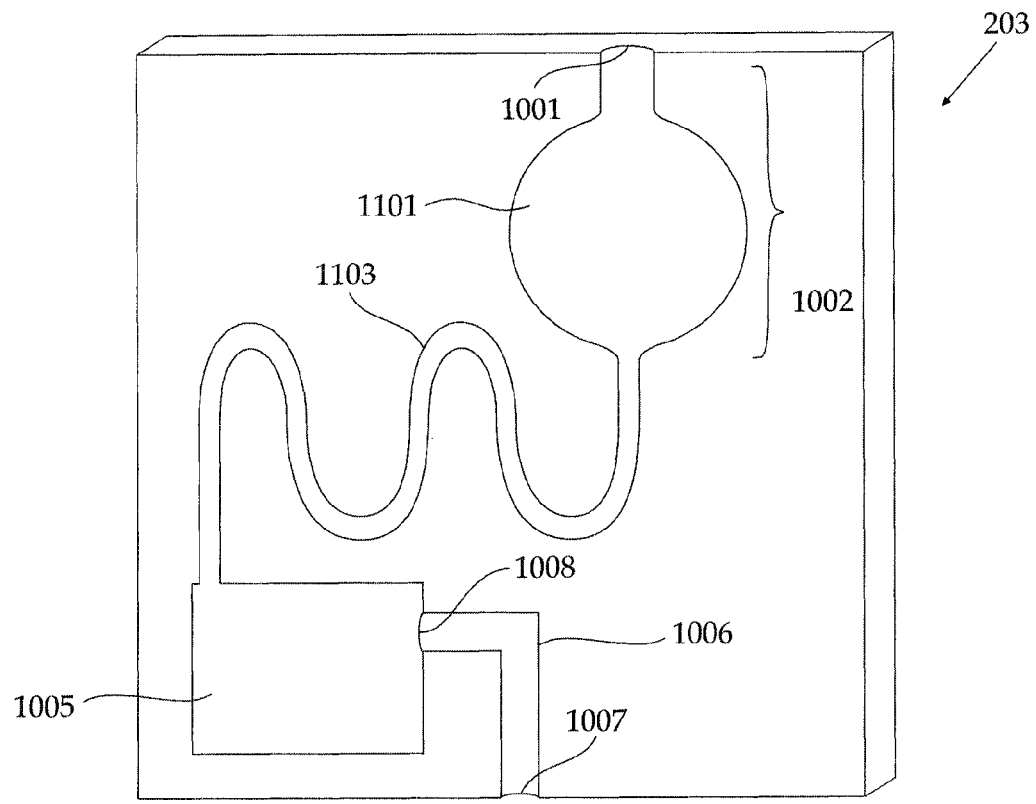
FIG. 11 schematically illustrates an alternative analyzing compartment, according to certain embodiments of the invention.

FIG. 11 schematically illustrates an alternative analyzing compartment, configured for determination of blood hemoglobin level, according to certain embodiments of the invention. This compartment too includes an analyzing unit comprises an analysis vessel 1002 which consists of an analyzing chamber 1101 coupled to a long small cross sectioned third channel 1103.

The analyzing chamber 1101 may contain a powdered oxidizing agent and/or a lysing agent. The agent may be Sodium Dodecyl Sulfate (SDS), TritonX or another oxidizing/lysing agent suitable for the case. When the chamber is filled with the output fluid, which in this case is a derivative of a blood sample, the oxidizing agent becomes dissolved. The dissolved oxidizing agent lyses the red blood cells of the derivative of the blood sample leading to release of hemoglobin. The released hemoglobin is then oxidated by the oxidizing agent to methemoglobin (which is a form of hemoglobin which cannot release bound oxygen). Concentration of methemoglobin is then determined using a spectrometer, by measuring an absorption of one or more wavelengths. That is, the analyzing module 105 of system 101 (see FIG. 1) should comprise a spectrometer, in this case.

According to certain embodiments, powdered agent may freely reside inside chamber 1101. Alternatively, it may coat the inner surface of the chamber 1101. For the purpose of enlarging the contact area between the agent and the derivative of the blood sample, according to certain embodiments the inner surface of the chamber may contain projections such as pillars, coated with the agent. Alternatively, for the same purpose, a powdered oxidizing agent may be attached to a carrier, such as sponge, filling the chamber.

Having understood this, it should be noted that a chamber containing coated projections is not limited to powdered oxidizing and/or lysing agents and/or to blood samples. A chamber having projections coated with a powdered agent, or even with other forms of agents such as gel, may be used in other occasions and situations wherein enlarging the contact area inside an analysis compartment's analysis vessel may be beneficial.

Those versed in the art would appreciate that the processes of cell lysis, hemoglobin oxidation and measuring an absorption require a certain minimal time interval each, Therefore, the derivative of the blood sample must be retained inside the analyzing chamber. According to embodiments of the invention, it is possible to achieve retention by applying high resistance to the flow, hence slowing it down. One way for applying such high resistance is by means of a long third channel 1003 having a small cross section coupled to the analyzing chamber 1101. When the channel is empty, no resistance to flow is present, therefore the derivative of the blood sample flows freely into the analysis vessel and the analyzing chamber via the third opening. However, filling the third channel with a derivative of the blood sample causes the resistance to raise, leading to a nearly complete cessation of flow.

Figure 12:
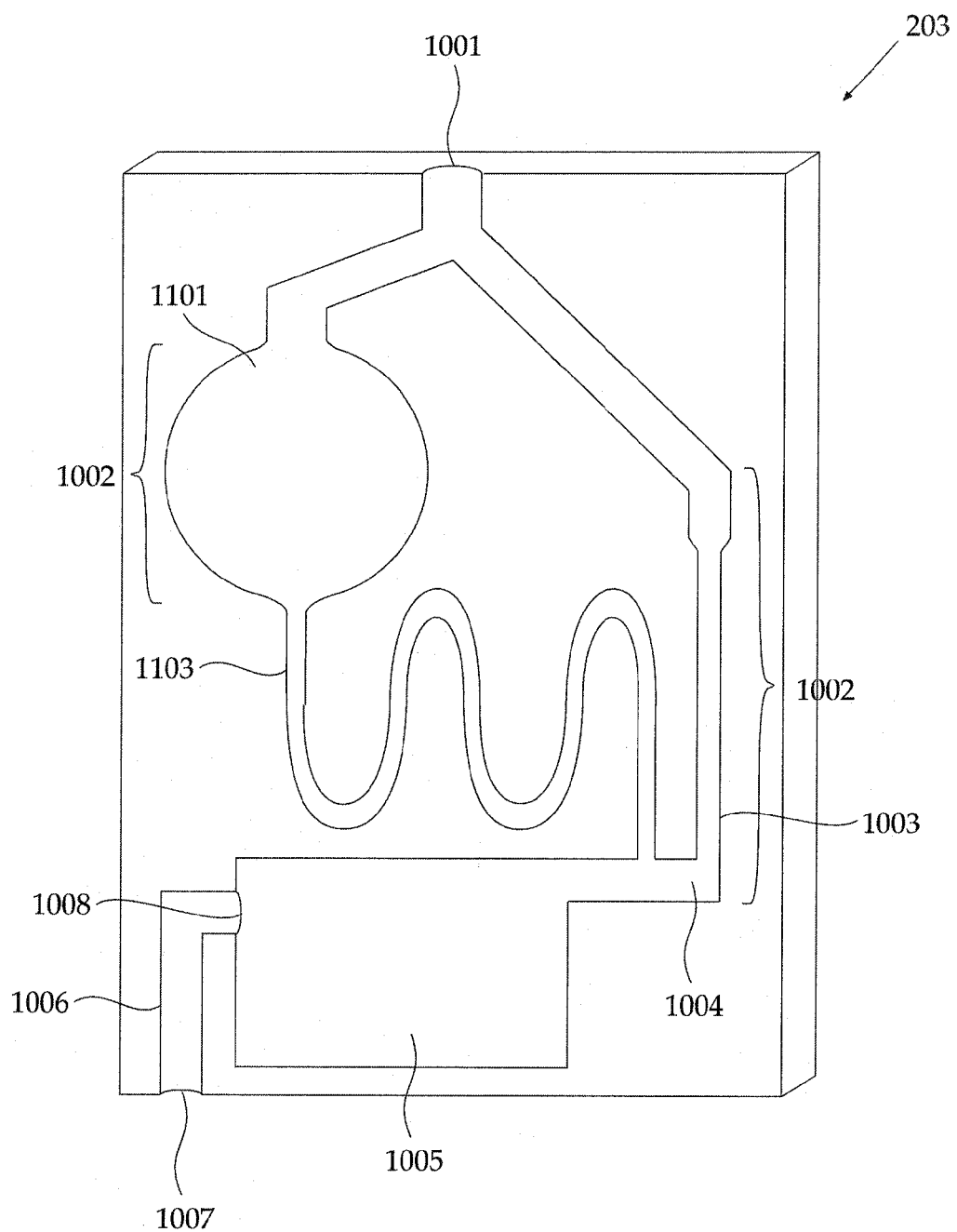
FIG. 12 schematically illustrates an analyzing compartment, comprising two analyzing units, according to certain embodiments of the invention.

FIG. 12 schematically illustrates an analyzing compartment, comprising two analyzing units, according to certain embodiments of the invention. One of the analytical units comprises a microchannel 1003, such as the analyzing unit depicted in FIG. 10 and described with reference thereto. The other analyzing unit comprises an analyzing chamber 1101, such as the analyzing unit depicted in FIG. 11 and described with reference thereto. According to such embodiments the two analyzing units may be coupled on one side to a third opening 1001 for purpose of obtaining the output fluid. On the other side they may be coupled to the waste container 1005, wherein disposable fluid may be disposed. That is, the two analyzing units are coupled in parallel.

It is noted that such parallel coupled analyzing units within an analyzing compartment enable to perform in parallel two separate types of analysis of the output fluid. For example, using the analytical compartment depicted by FIG. 12 cell counting and measuring of hemoglobin level of a derivative of a blood sample may be performed. It is worth noting, that the two types of analysis are performed using different analyzing modules 105 in system 101 (see FIG. 1), e.g., a camera and a spectrometer.

Figure 13A:
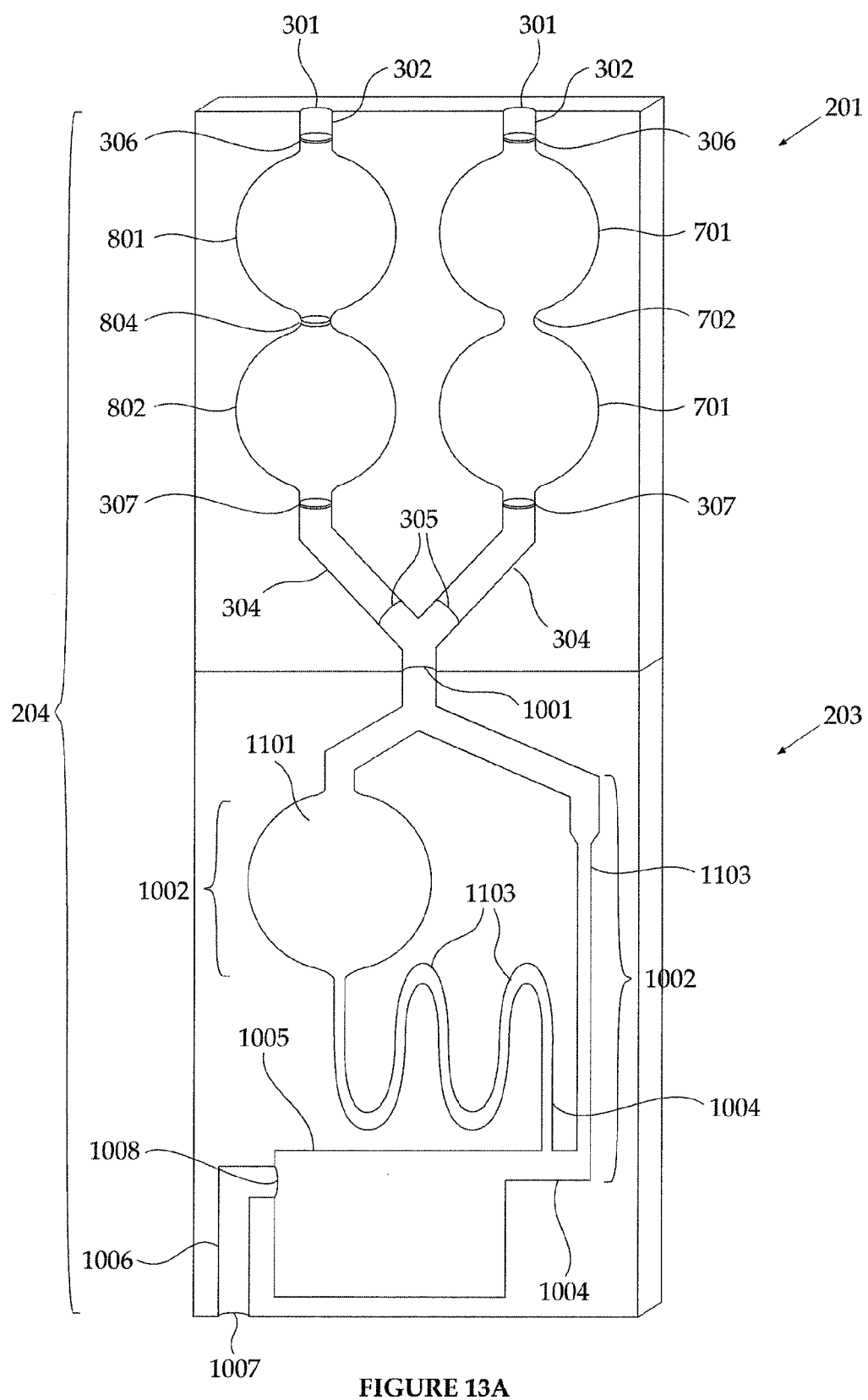
FIGS. 13A and 13B schematically illustrate a cartridge comprising a preparation compartment and an analyzing compartment, according to different embodiments of the invention.
Figure 13B:
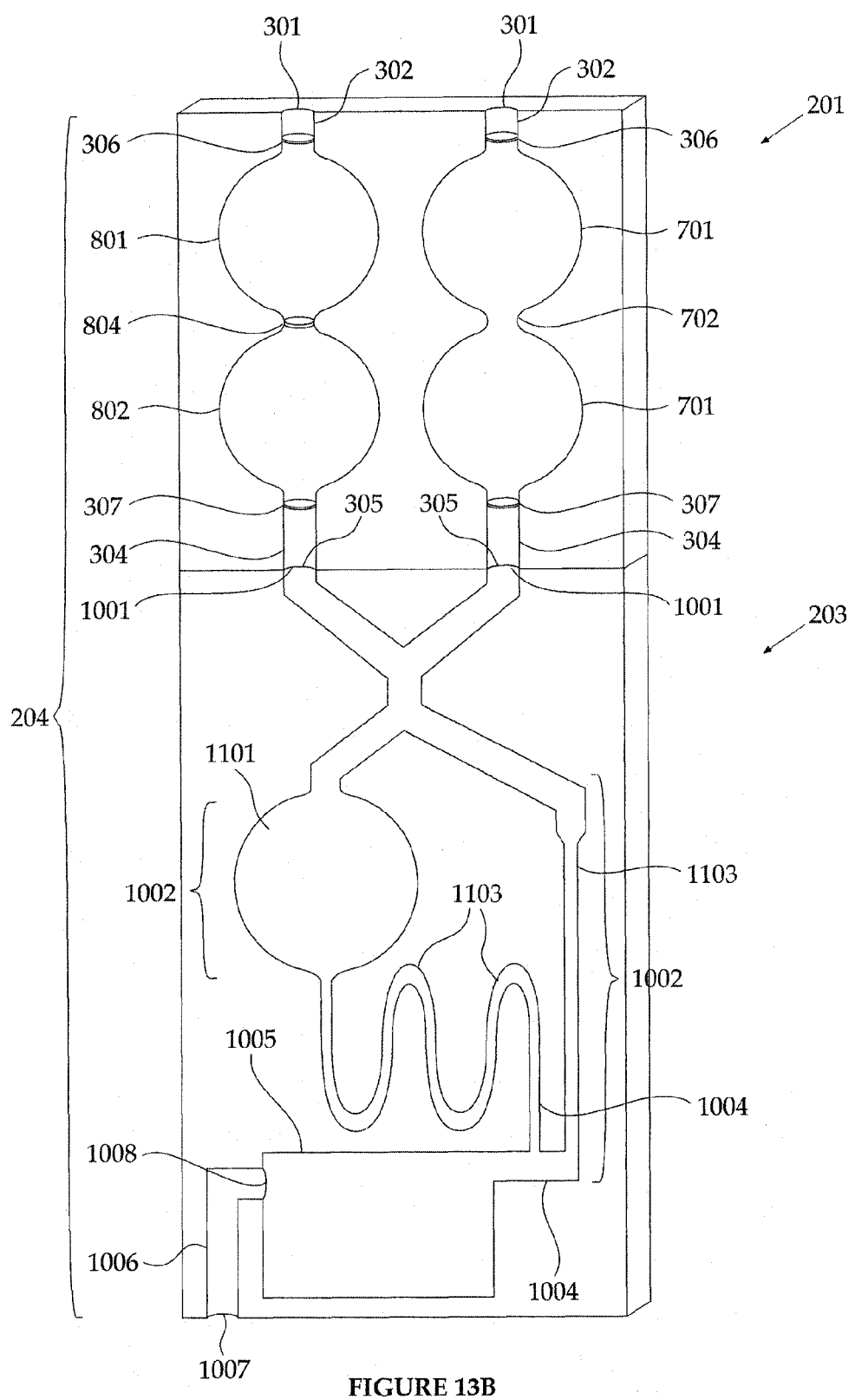

FIGS. 13A and 13B schematically illustrate a cartridge comprising a preparation compartment and an analyzing compartment, according to certain embodiments of the invention.

In has been stated above, with reference to FIG. 2 that in some embodiments the analyzing compartment 203 coupled to the cartridge 201, is not a part thereof, while in other embodiments the analyzing compartment 203 may be considered as part of the cartridge. According to such embodiments 201 relates to a "preparation compartment" while a cartridge 204 may be composed of a preparation compartment 201 and an analyzing compartment 203. To this end, and due to simplicity consideration, FIGS. 13A and 13B are presented and described wherein a cartridge 204 has a preparation compartment 201 and an analysis compartment 203. However, this is non-limiting and the description applies also to the other convention, wherein 201 is the cartridge.

Two different embodiments of cartridge 204 are depicted by FIGS. 13A and 13B. First, the description of features common to both configurations is brought, and then, dissimilarities therebetween shat be discussed.

The preparation compartment 201 of the cartridge 204 has been described in detail above, with reference to FIGS. 9A and 9B. In the example presented in FIGS. 13A and 13B, the preparation compartment comprises two preparation units, the first unit and the second unit. The first preparation unit, comprising a single chamber (e.g., a mixing chamber) containing two interconnected compartments 701, has been described in detail above, with reference to FIG. 7. The second preparation unit, comprising two chambers 801 (e.g., a first reagent chamber) and 802 (e.g., a second reagent chamber), has been described in detail above, with reference to FIG. 8.

The analyzing compartment 203 of a cartridge 204 has been described in detail above, with reference to FIG. 12. The analyzing compartment contains two analyzing units. One of the analyzing units, comprising a microchannel 1003, is configured to align cells contained in the output fluid into a single plane allowing taking images of the flowing cells using a camera, or probed by a focused light beam/laser beam as done in a cytometer. This analysing unit has been described in detail above, with reference to FIG. 10. The other analyzing unit, comprising an analyzing chamber 1101 coupled to a long small cross-sectioned third channel 1004, is configured for determination of hemoglobin level, e.g., using a spectrometer. This analysing unit has been described in detail above, with reference to FIG. 11.

To allow flow of the output fluid prepared for analysis from the preparation compartment to the analysis compartment the two compartments are interconnected by means of the second opening of the preparation compartment coupled to the third opening of the analyzing compartment. The two configurations of the cartridge, depicted by FIGS. 9A and 9B, differ respective to a number and position of the second openings of the preparation compartment and correspondingly the coupled thereto third openings of the analyzing compartment. Thus, in the cartridge depicted by FIG. 13A there is a single second opening 901 of preparation compartment 201, connected to the second openings 305 of both preparation units. The single second opening 901 of the preparation unit is coupled to a single third opening 1001 of the analyzing compartment. In contrast, in the cartridge depicted at FIG. 13B the second openings 305 of both preparation units form also second openings of the preparation unit, and they are directly coupled to the respective two third openings 1001 of the analyzing compartment.

According to certain embodiments of the invention the cartridge 204 is configured to allow a performance of blood count, while a sample fluid introduced into the cartridge is a blood sample. A blood count performed by the cartridge may include determination of number of red blood cells, white blood cells (total count) and platelets present in the sample, as well as determination of number of each one the of white blood cell types (differential count). The white blood cell types may be neutrophils, lymphocytes, monocytes, eosinophils and monocytes or part thereof. Those versed in the art would appreciate that there are additional types and sub-types of white blood cells, and therefore the invention is not limited to the types mentioned. Furthermore, the invention is not limited to the blood cells mentioned and it may be applicable to any type of cells circulating in the blood, including, e.g., circulating tumor cells, platelets aggregates and others.

Attention is drawn now to describing in detail the processes of preparation of a blood sample for analysis, whereas the analysis is a blood count.

In the described embodiments of the invention, cells counting may be performed by means of acquiring images of flowing cells by a camera or by probing by a focused light beam/laser beam as done in a cytometer. In order to allow reliable counting, the cells mast be brought into the focal place of the optics. Hence, the cells should be aligned in a single plane, e.g., by viscoelastic focusing. The method is based on suspending cells in a focusing medium of certain viscoelastic properties causing the cells suspended therein to align into a single plane if being flowed in a microchannel of a certain geometry. Therefore preparing a sample fluid for counting, performed in preparation compartment 201 of a cartridge 204, includes adding focusing media to the sample fluid, thus yielding a derivative of the sample fluid. This however is not-limiting and in different embodiments cells may be aligned using other methods, whereas preparing a sample fluid for counting, performed in a preparation unit of a cartridge, may include different procedures.

The first preparation unit is configured for preparing a blood sample for determination of number of red blood cells, white blood cells (total count) and platelets present therewithin. A substance contained in chamber 701 comprises focusing medium with addition of surfactants. The focusing medium comprises a buffer containing soluble high molecular weight polymers. The buffer may be any isotonic buffer suitable for managing living cells, for example it may be Phosphate Buffered Saline (PBS). Examples of soluble polymers suitable for providing the blood sample with viscoelastic properties are polyacrylamide (PAA), polyethyleneglycol (PEG), Propylene Glycol, etc. The surfactants added to a focusing media act as sphering agents, i.e., they cause the shape of red blood cells to change from biconcave discs into spheres, allowing to obtain better images of cells. Examples of surfactants are SDS (Sodium Dodecyl Sylphate) and DDAPS (dodecyldimethylammoniopropanesulfonate). The composition of the focusing medium is disclosed, e.g., in PCT Publication No. WO2008/149365 entitled "Systems and Methods for Focusing Particles".

The procedure performed by chamber 701 is mixing of the delivered blood sample with a focusing medium. After mixing has been completed the succeeding seal 305 becomes breached by pressure, allowing the generated output fluid to flow into the analytical compartment.

The second preparation unit is configured for preparing a blood sample for differential count of white blood cell types. In certain embodiments of the invention the preparation includes chemical staining of cells, whereas two consecutive staining procedures are performed in chambers 801 and 802 of the preparation unit.

The substance contained in chamber 801 may comprise cell staining reagents dissolved in the focusing medium. Examples for cell staining reagents are Phloxine B, Biebrich Scarlet and Basic Orange 21. As a fixation of cells may be needed in some cases, fixating reagents, for example formaldehyde or formalin, may also be contained. Following mixing of the blood sample with the substance, an incubation may be performed, allowing staining. Upon expiration of a predetermined incubation time a seal 804 separating the chamber 801 from the chamber 802 becomes breached by pressure, resulting in release of the generated output fluid towards the chamber 802.

The substance contained in chamber 802 may comprise other cell staining reagents dissolved in the focusing medium. Examples for cell staining reagents are Methyl Green, Methylene Blue and Borrel's Blue. Following mixing of an input fluid (which constitutes the output fluid of chamber 801) with a substance, a second incubation may be performed, allowing the second staining process to occur. Upon expiration of a second predetermined incubation time the succeeding seal 307 of the second preparation unit becomes breached by pressure allowing generated output fluid to flow into the analytical compartment.

In other embodiments of the invention preparing cells for analysis includes immuno-based staining of the cells. In these embodiments one or both chambers of the preparation unit contain reagents suitable for immune-staining, whereas the reagents and the focusing medium may be contained within a single chamber or in different chambers. Examples of reagents suitable for immune-staining are antibody-coated micro beads of different colors, such as CD14/CD15 and a combination of stains.

Attention is turned now to a detailed description of the process of presentation for analysis of the output fluid of the preparation units, whereas the analysis is blood count.

The output fluids flowing out of the second openings 305 of both preparation units are conveyed to a single channel that is coupled to the analysis vessels of both analyzing units. Analysis of the output fluids is performed sequentially. The sequentially analysis is enabled by temporal separation of the two output fluids, a separation controlled in the preparation compartment. As described above the preparation process performed by a first preparation unit includes mixing in a single chamber without incubation, while the preparation process performed by a second preparation unit includes, in addition to mixing in two different chambers, two staining procedures that might require incubation time. Hence, the output fluid of the first preparation unit is ready to flow into the analyzing compartment before the output fluid of the second preparation unit is ready.

Upon flowing into the analyzing compartment 203 the output fluid of the first preparation unit is divided between the two illustrated analyzing units. Part of the fluid enters the microchannel 1003, wherein the cells within the output fluid become aligned into a single plane in a way explained with reference to FIG. 10. The aligned cells may then be optically analyzed, through a transparent or translucent surface of the microchannel. The output fluid then flows into waste container 1003, wherein it is stored.

The other part of the output fluid enters the analyzing chamber 1101, wherein the cells within the output fluid become lyzed and their hemoglobin content quantified in a way described in reference to FIG. 11.

The flow of the output fluid of the first preparation unit into the analyzing compartment must be aborted prior to breaching the succeeding seal 307 of the second preparation unit, to prevent mixing of the output fluids that will hamper analysis. This is enabled due the second channel 304 of the first preparation unit being re-sealable. The re-sealing of the channel may be performed, for example, by pressure applied to the succeeding seal or to another area of the second channel.

The long and small cross-sectioned third channel 1103 coupled to chamber 1101, enhances resistance to flow at the chamber. Hence, upon breaching succeeding seal 307 of the second preparation unit, the substantially all the output fluid flows into the analyzing compartment and conveyed to the microchannel 1003 Instead of being split between the two analysis units. Inside the microchannel 1003 the cells within the output fluid of the second preparation unit become aligned into a single plane hence allowing optical analyzed. The output fluid then flows into the waste container, wherein it is stored.

It is further noted that in FIGS. 10-13B, the waste container 1005 appears to be in the analyzing compartment 203. Yet, this is non-mandatory. It was previously explained, with reference to FIG. 2, that the analyzing compartment 203 may be positioned in a gap, or a window, inside the cartridge. In such embodiments the cartridge may comprise the waste container, wherein in such embodiments an opening in the third channel 1004 would be used for interfacing the third channel in the analyzing module with the waste container in the cartridge or with a channel leading thereto.

Figure 14A:
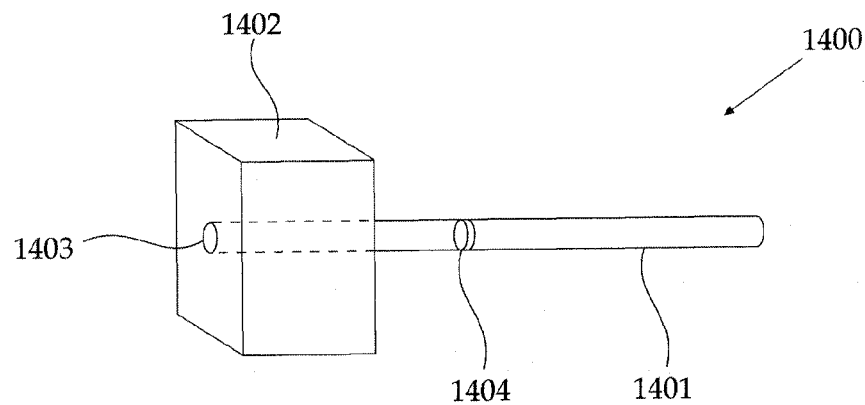
FIGS. 14A, 14B and 14C schematically depict samplers according to certain embodiments of the invention.
Figure 14B:
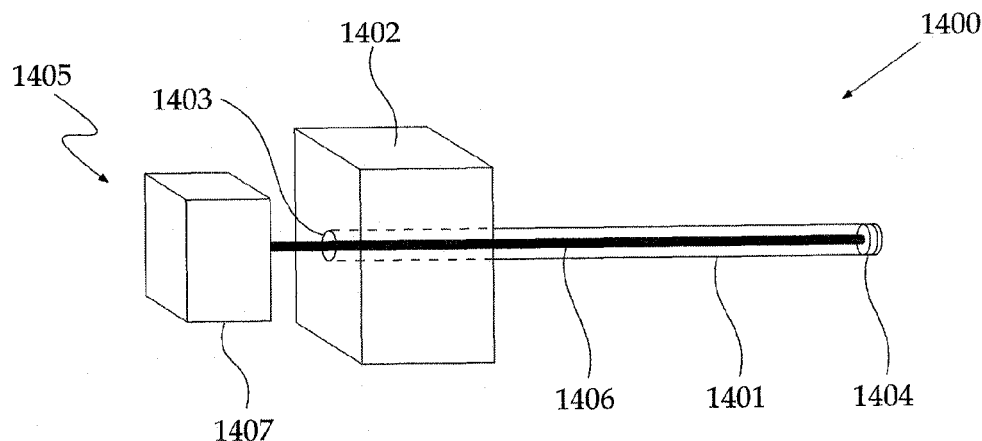
Figure 14C:
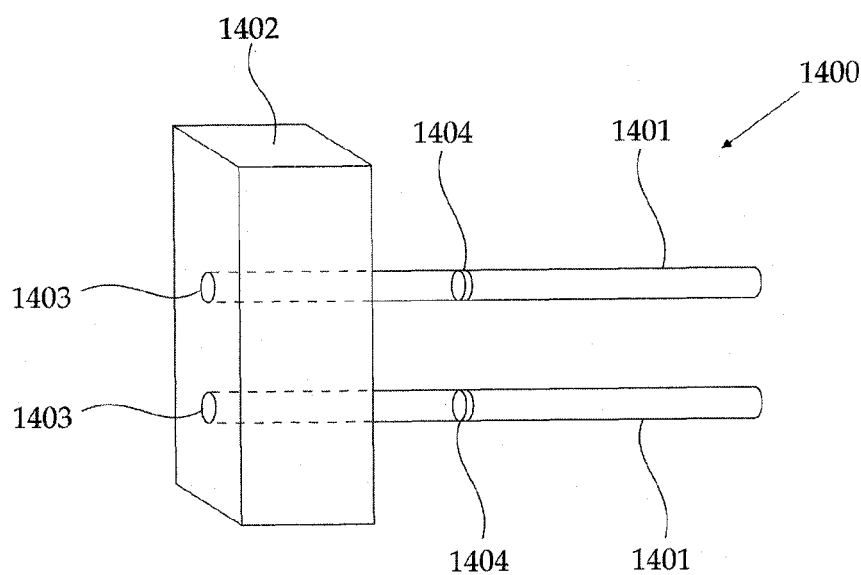

Having understood the structure and functionality of a cartridge, in accordance with certain embodiments of the invention, a sampler is now described. FIGS. 14A, 14B and 14C, schematically depict samplers, according to certain embodiments of the invention. A sampler 1400 is configured to sample fluid and to introduce it into the cartridge 204. The sampler depicted by 14A comprises a carrier 1401, attached to a handle 1402. In the described non-limiting embodiment the carrier is a capillary. Inside the capillary a hydrophobic membrane 1404 is affixed in a pre-determined distance from the capillary outlet. The capillary 1401 might be any type of capillary with a hydrophobic membrane affixed inside and suitable for the case, for example capillaries manufactured by DRUMMOND Aqua-Cap™ Microdispenser.

It is noted though that the hydrophobic membrane 1404 does not limit the invention and other mechanisms are allowed for ensuring that the amount of sample fluid in the capillary is precise. For example: it is possible to use a shorter capillary whose volume is the precise required volume. Alternatively, another constriction element can be used instead of the membrane, such as an orifice.

Fluid sampling is performed by immersing the outlet of the capillary 1401 in the fluid. A person versed in the art would appreciate that the fluid is driven into the capillary by capillary force. The hydrophobic membrane 1404 affixed inside the capillary 1401 does not interfere with the process, as it allows the air displaced by a driven inside fluid to flow out. The fluid fills the capillary until reaching the hydrophobic membrane. It should be appreciated that due to the hydrophobic nature of membrane 1404, the fluid does not come into contact therewith. Therefor there is no sample fluid absorbance in the membrane, or in other words, no loss of fluid volume occurs in favor of the membrane. Hence the final volume of a sampled fluid is determined by a distance of the hydrophobic membrane 1404 from the capillary outlet and by the capillary's diameter.

Once the fluid has been sampled it is delivered, introduced, into the cartridge 204 by inserting the capillary 1401 through the first opening 301 thereof. At this stage only a limited leakage of a sample fluid from the capillary into a chamber 303 occurs, as the fluid is being held inside by capillary forces. Next, a plunger 1405 is used to push the sampled blood out of the capillary into the chamber 303. The plunger 1405, depicted in FIG. 14B comprises a plunging member 1406 attached to a holding member 1407. The plunging member 1406 is configured to be inserted into the capillary 1401 through a capillary inlet 1403 located in the handle 1402. The plunger pushes the hydrophobic membrane 1404 until it reaches the capillary outlet, optionally resulting in the delivery of the entire sample fluid into the chamber 303. It should be considered though that if the plunging member 1406 is not long enough for reaching the capillary outlet, a certain dose of fluid will remain in the capillary. Hence the volume of the sample fluid delivered into the chamber is determined by a length of a plunging member 1406 of a plunger 1405. The capillary's diameter is known in advance, and so is the length of the capillary as well as the length of the plunger. Hence, the volume of the fluid transferable by the sampler can be predetermined.

It must be appreciated that the mechanisms of sampling and plunging described above enable delivery into the chamber of a fixed volume of sample fluid. The ability to deliver a fixed volume of a fluid is very important, as any deviation in the delivered volume may affect the reliability of the sequential analysis. Moreover there is no need to flush the blood out of the carrier (in this case the capillary) as is the case in other applications because the hydrophobic membrane thoroughly dispenses all the blood into the first chamber.

With reference to certain embodiments, the plunger 1405 is a part of analyzing system 101, whereas the plunger is inserted into the cartridge 204 upon placement thereof inside the cartridge holding unit 103 of an analyzing system 101. However, in different embodiments the plunger may constitute a separate device, whereas the insertion of a plunger into the cartridge may be performed prior to placement thereof into the cartridge holding unit 103.

In different embodiments, illustrated by FIG. 14C, the sampler is comprised of two carriers 1401, wherein sampling of the fluid by the carriers is performed sequentially. However, this is not limiting and embodiments in which sampling of the fluid by the carriers is performed simultaneously may exist.

The sampler comprising two carriers may be used, such as the one illustrated in FIG. 14C, for sampling and delivery of blood into a cartridge configured to allow performance of blood count, such as the cartridge described above with reference to FIG. 13. Sometimes, the two carriers of the sampler may comprise anticoagulant-coated capillaries with a hydrophobic membrane. An anticoagulant, coating the capillaries, serves to prevent clotting of sampled blood. An example of an anticoagulant is EDTA (Ethylenediaminetetraacetic acid).

It must be appreciated that a fluid volume sampled by each carrier 1401 of the sampler 1400 and delivered into the cartridge 204 may be as small as 20 µl and possibly even less. Therefore, performance of a blood count using the sampler 1400, the cartridge 204 and the analyzing system 101 requires obtaining of as little as a single drop of blood from the individual. Such a small volume of blood may be obtained by pricking the fingertip or forearm in a way performed for example by home blood glucose monitoring devices, thus sparing driving blood from a vein, which is less convenient for patients, especially children.

The invention claimed is:

1. A disposable cartridge, comprising:
   an inlet configured to receive a sample fluid that includes blood;
   a first reagent chamber wherein at least a portion of a surface of the first reagent chamber comprises a pressable portion;
   a first reagent pre-loaded and sealed within the first reagent chamber;
   a second reagent chamber wherein at least a portion of a surface of the second reagent chamber comprises a pressable portion;
   a second reagent pre-loaded and sealed within the second reagent chamber;
   a flow channel interconnecting the first reagent chamber and the second reagent chamber, the flow channel, the first reagent chamber, and the second reagent chamber defining a flow path;
   wherein a first frangible seal prevents flow between the first reagent chamber and the second reagent chamber;
   the first frangible seal configured to open in response to pressure applied by contents of one of the reagent chambers against the first frangible seal;
   wherein the cartridge is configured so that when the first frangible seal opens, the first reagent contacts the second reagent; and
   a mixing chamber, wherein a fluid substance is pre-loaded and sealed within the mixing chamber.

2. The disposable cartridge of claim 1, wherein the cartridge further comprises another frangible seal associated with the mixing chamber, the another frangible seal configured to open in response to pressure above a predetermined threshold exerted on the mixing chamber.

3. The disposable cartridge of claim 1, further comprising:
   the second reagent chamber being coupleable to an analyzing unit, which performs analysis of an output fluid; and
   a second frangible seal preventing flow between the second reagent chamber and the analyzing unit,
   wherein the first and second frangible seals are configured to open at different times.

4. The disposable cartridge of claim 1, wherein at least one of the first and second reagent chambers is coupleable to an analyzing unit, which performs analysis of an output fluid.

5. The disposable cartridge of claim 1, wherein a second frangible seal in the flow path is configured to prevent the first or second reagent from flowing out of the second reagent chamber when the second frangible seal is intact.

6. The disposable cartridge of claim 1, wherein at least one of the first reagent and the second reagent includes at least one high molecular weight polymer in fluid form.

7. The disposable cartridge of claim 1, wherein the first reagent chamber includes an inlet seal configured to prevent the first reagent from flowing via the inlet when the inlet seal is intact.

8. The disposable cartridge of claim 7, wherein the inlet seal comprises a re-sealable seal.

9. The disposable cartridge of claim 1, wherein at least one of the first and second reagent chambers is configured to convey an output fluid to an analyzing unit via an opening.

10. The disposable cartridge of claim 9, wherein a second frangible seal in the flow path is configured to prevent the first or the second reagent from flowing via the opening when the second frangible seal is intact.

11. The disposable cartridge of claim 1, further comprising:
    at least one of the first reagent chamber and the mixing chamber being provided with an entry sealing member, wherein
    the entry sealing member prevents at least one of the first reagent and fluid substance from flowing out of the at least one of the first reagent chamber and the mixing chamber via the inlet when the entry sealing member is intact, the entry sealing member configured to be punctured by a capillary tube, and wherein
    the entry sealing member is configured to seal around a circumference of the capillary tube that punctures the entry sealing member and is inserted into the at least one of the first reagent chamber and the mixing chamber.

12. The disposable cartridge of claim 11, wherein the entry sealing member comprises:
    an inlet seal and a capillary seal,
    wherein the inlet seal prevents the at least one of the first reagent and fluid substance from flowing out of the at least one of the first reagent chamber and the mixing chamber via the inlet when the inlet seal is intact, the inlet seal configured to be punctured by the capillary tube, and wherein
    the capillary seal is configured to seal around the circumference of the capillary tube inserted through the capillary seal and into the at least one of the first reagent chamber and the mixing chamber.

13. The disposable cartridge of claim 11, wherein the mixing chamber comprises at least a first compartment and a second compartment, wherein a narrow passage of the mixing chamber interconnects the first compartment to the second compartment.

14. A cartridge assembly including the disposable cartridge of claim 1, further comprising:
    a capillary tube configured to introduce the sample fluid into the cartridge via the inlet;
    wherein at least one of the first reagent chamber and the mixing chamber is provided with an entry sealing member;
    wherein the entry sealing member prevents at least one of the first reagent and fluid substance from flowing out of the at least one of the first reagent chamber and the mixing chamber via the inlet when the entry sealing member is intact;
    wherein the capillary tube is configured to puncture the entry sealing member by inserting the capillary tube beyond a position of the entry sealing member; and
    wherein the entry sealing member is configured to seal around a circumference of the capillary tube when the capillary tube is inserted into the at least one of the first reagent chamber and the mixing chamber.

15. The cartridge assembly of claim 14, wherein the mixing chamber comprises at least a first compartment and a second compartment, wherein a narrow passage of the mixing chamber interconnects the first compartment to the second compartment.

16. The cartridge assembly of claim 14, further comprising:
the second reagent chamber being coupleable to an analyzing unit, which performs analysis of an output fluid; and
a second frangible seal preventing flow between the second reagent chamber and the analyzing unit,
wherein the first and second frangible seals are configured to open at different times.

17. The cartridge assembly of claim 14, wherein at least one of the first reagent and the second reagent includes at least one high molecular weight polymer in fluid form.

18. The cartridge assembly of claim 14, wherein the entry sealing member comprises:
an inlet seal and a capillary seal,
wherein the inlet seal prevents the at least one of the first reagent and fluid substance from flowing out of the at least one of the first reagent chamber and the mixing chamber via the inlet when the inlet seal is intact, the inlet seal configured to be punctured by the capillary tube, and wherein
the capillary seal is configured to seal around the circumference of the capillary tube inserted through the capillary seal and into the at least one of the first reagent chamber and the mixing chamber.

19. The cartridge assembly of claim 18, wherein the inlet seal and capillary seal are provided in succession within the inlet.

20. The cartridge assembly of claim 14, wherein the capillary tube is coated with an anticoagulant.

21. The cartridge assembly of claim 20, wherein the anticoagulant is ethylenediaminetetraacetic acid.

22. The cartridge assembly of claim 14, further comprising:
the capillary tube having a first end and a second end; and
a barrier positioned within the capillary tube, wherein the barrier is configured to allow air inside of the capillary tube to exit a second end of the capillary tube as the sample fluid flows into the capillary tube through the first end and displaces the air inside of the capillary tube, and wherein the barrier prevents passage of the sample fluid.

23. The cartridge assembly of claim 22, wherein the barrier is a hydrophobic membrane.

24. The cartridge assembly of claim 23, wherein the hydrophobic membrane does not absorb the sample fluid.

25. The cartridge assembly of claim 22, wherein, after the sample fluid flows into the capillary tube through the first end,
subsequent movement of the barrier towards the first end is configured to expel a predetermined volume of the sample fluid into the at least one of the first reagent chamber and the mixing chamber.

26. A system including the cartridge assembly of claim 25, further comprising:
a plunger inserted into the second end of the capillary tube and advanced towards the first end of the capillary tube, thereby causing the subsequent movement of the barrier towards the first end and the expelling of the sample fluid into the at least one of the first reagent chamber and the mixing chamber.

* * * * *